(12) United States Patent
Yoo et al.

(10) Patent No.: US 11,690,291 B2
(45) Date of Patent: Jun. 27, 2023

(54) ORGANIC COMPOUND, AND ORGANIC LIGHT EMITTING DIODE AND ORGANIC LIGHT EMITTING DISPLAY DEVICE INCLUDING THE SAME

(71) Applicant: LG DISPLAY CO., LTD., Seoul (KR)

(72) Inventors: Seon-Keun Yoo, Gunpo-si (KR); Sung-Hoon Joo, Paju-si (KR); Seung-Hee Yoon, Seoul (KR); Ji-Cheol Shin, Seoul (KR)

(73) Assignee: LG DISPLAY CO., LTD., Seoul (KR)

( * ) Notice: Subject to any disclaimer, the term of this patent is extended or adjusted under 35 U.S.C. 154(b) by 242 days.

(21) Appl. No.: 17/101,701

(22) Filed: Nov. 23, 2020

(65) Prior Publication Data

US 2021/0074928 A1 Mar. 11, 2021

Related U.S. Application Data

(63) Continuation of application No. 15/639,622, filed on Jun. 30, 2017, now Pat. No. 10,879,472.

(30) Foreign Application Priority Data

Jun. 30, 2016 (KR) .................. 10-2016-0082776

(51) Int. Cl.
| | |
|---|---|
| *H01L 51/00* | (2006.01) |
| *C07D 471/04* | (2006.01) |
| *H10K 85/60* | (2023.01) |
| *H05B 45/60* | (2022.01) |
| *H10K 50/16* | (2023.01) |
| *H10K 50/19* | (2023.01) |
| *H10K 50/81* | (2023.01) |
| *H10K 50/82* | (2023.01) |
| *H10K 50/13* | (2023.01) |
| *H10K 59/12* | (2023.01) |

(52) U.S. Cl.
CPC ....... *H10K 85/6572* (2023.02); *C07D 471/04* (2013.01); *H10K 85/615* (2023.02); *H10K 85/622* (2023.02); *H10K 85/626* (2023.02); *H10K 85/654* (2023.02); *H05B 45/60* (2020.01); *H10K 50/131* (2023.02); *H10K 50/16* (2023.02); *H10K 50/19* (2023.02); *H10K 50/81* (2023.02); *H10K 50/82* (2023.02); *H10K 59/12* (2023.02)

(58) Field of Classification Search
None
See application file for complete search history.

(56) References Cited

U.S. PATENT DOCUMENTS

2007/0231503 A1  10/2007  Hwang et al.

FOREIGN PATENT DOCUMENTS

| CN | 104039773 A | 9/2014 |
|---|---|---|
| CN | 105321984 A | 2/2016 |
| CN | 105679950 A | 6/2016 |
| EP | 2983227 A1 | 2/2016 |

(Continued)

*Primary Examiner* — Jay Yang
(74) *Attorney, Agent, or Firm* — Birch, Stewart, Kolasch & Birch, LLP

(57) ABSTRACT

Embodiments of the present invention provide an organic light emitting diode and an organic light emitting display device including the organic compound. The organic compound is capable of reducing a driving voltage of an organic light emitting diode and improves a current efficiency and a lifetime of the organic light emitting diode and the organic light emitting display device including the same.

18 Claims, 9 Drawing Sheets
(6 of 9 Drawing Sheet(s) Filed in Color)

(56) References Cited

FOREIGN PATENT DOCUMENTS

| | | |
|---|---|---|
| EP | 3032605 A1 | 6/2016 |
| KR | 10-2015-0054797 A | 5/2015 |
| KR | 10-2015-0124000 A | 11/2015 |
| KR | 10-2017-0105040 A | 9/2017 |
| WO | WO 2016/121597 A1 | 8/2016 |

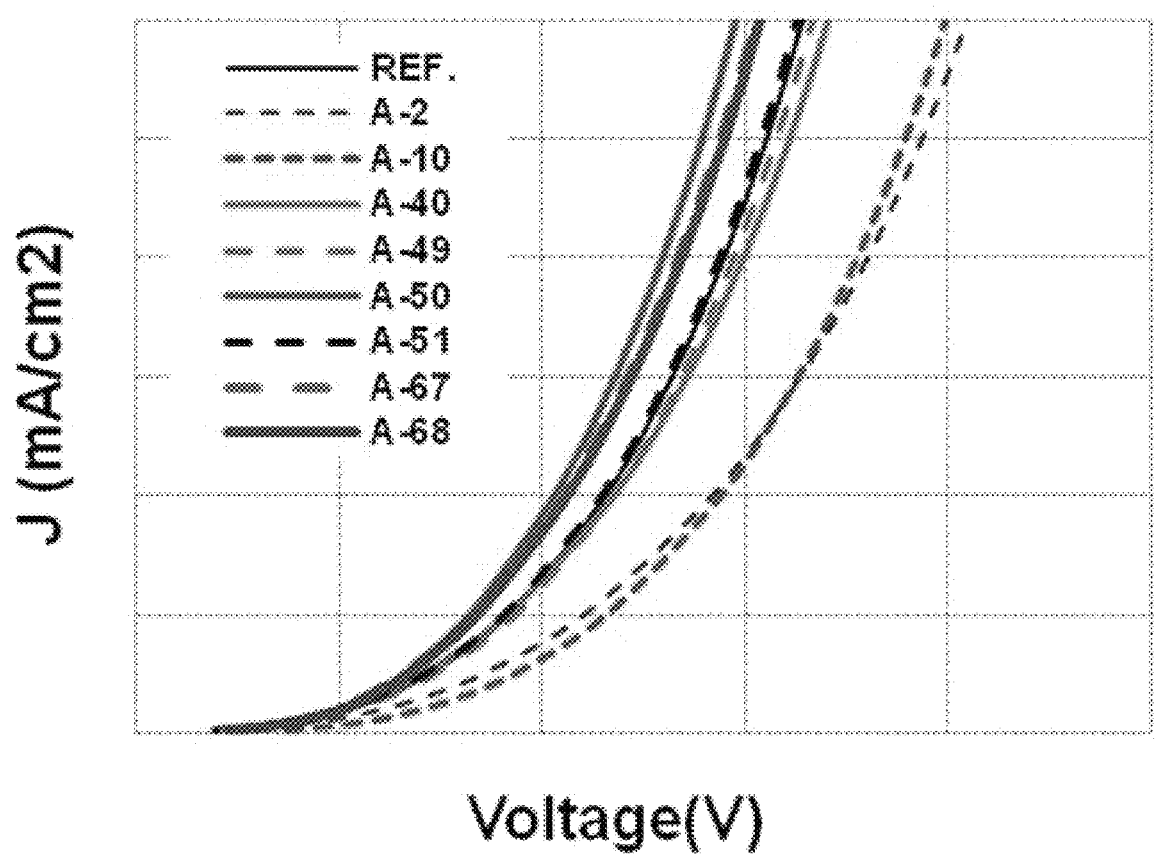

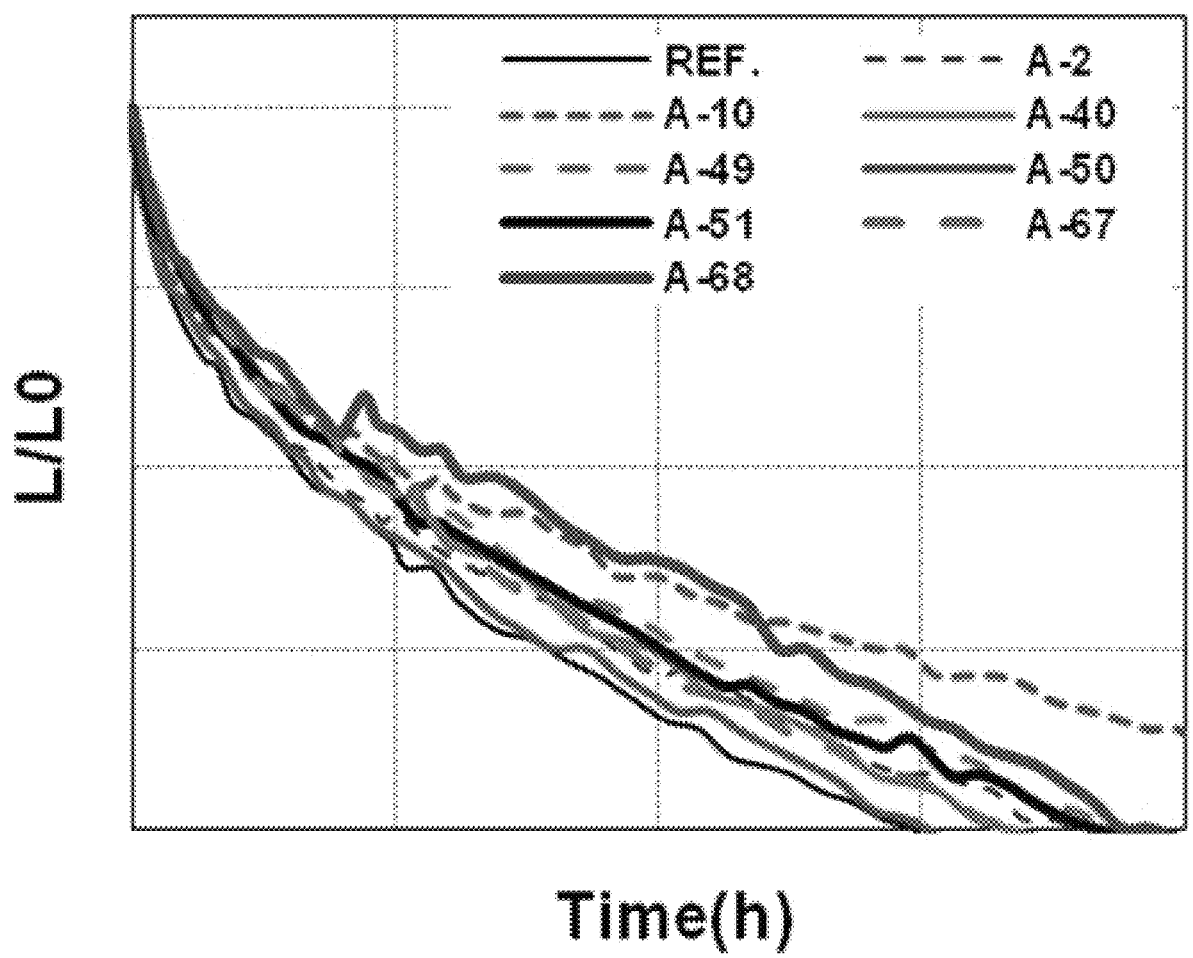

ORGANIC COMPOUND, AND ORGANIC LIGHT EMITTING DIODE AND ORGANIC LIGHT EMITTING DISPLAY DEVICE INCLUDING THE SAME

CROSS-REFERENCE TO RELATED APPLICATIONS

This application is a Continuation of co-pending U.S. patent application Ser. No. 15/639,622, filed on Jun. 30, 2017, which claims priority under 35 U.S.C. § 119(a) to Korean Patent Application No. 10-2016-0082776, filed in Republic of Korea on Jun. 30, 2016, all of these applications are hereby expressly incorporated by reference into the present application.

BACKGROUND OF THE INVENTION

Field of the Invention

The present invention relates to an organic compound and more particularly to an organic compound being capable of reducing a driving voltage of an organic light emitting diode and improving a current efficiency and a lifetime of the organic light emitting diode and the organic light emitting display device including the organic compound.

Discussion of the Related Art

As requests for a flat panel display device having a small occupied area have increased, an organic light emitting display (OLED) device including an organic light emitting diode has been the subject of recent research.

The organic light emitting diode emits light by injecting electrons from a cathode as an electron injection electrode and holes from an anode as a hole injection electrode into an emission compound layer, combining the electrons with the holes, generating an exciton, and transforming the exciton from an excited state to a ground state. A flexible substrate, for example, a plastic substrate, can be used as a base substrate where elements are formed. Since the OLED does not require a backlight assembly, the OLED has low weight and low power consumption. Moreover, the OLED can be operated at a voltage (e.g., 10V or below) lower than a voltage required to operate other display devices.

On the other hand, a white organic light emitting diode are used for a lighting apparatus, a thin light source, a backlight unit of a liquid crystal display device and a full color display device including a color filter.

In the white organic light emitting diode, properties of color purity, color stability, emitting efficiency and lifetime are important considerations. For example, the white organic light emitting diode may be classified into a single-layered emission structure and a multi-layered emission structure. To obtain a long lifetime white organic light emitting diode, the white organic light emitting diode having a stack structure of a fluorescent blue emitting layer and a phosphorescent yellow emitting layer may be used. This structure may be referred to as a tandem structure.

For example, the tandem structure white organic light emitting diode may include a first emitting part including a fluorescent blue emitting layer and a second emitting part including a phosphorescent yellow-green emitting layer. The first and second emitting parts may be vertically stacked. In the above tandem structure white organic light emitting diode, the light from the fluorescent blue emitting layer and the light from the phosphorescent yellow-green emitting layer are mixed to provide the white light.

To increase the current efficiency and improve the charge distribution, the tandem structure white organic light emitting diode further includes a charge generation layer between the first and second emitting parts. The charge generation layer (CGL) may have a P-N junction structure of an N-type CGL and a P-type CGL.

However, in the related CGL, the charge is generated at an interface between the P-type CGL and a hole injection layer (HIL) or between the P-type CGL and a hole transporting layer (HTL) because of an energy difference between the N-type CGL and the P-type CGL. As a result, an electron injection property into the N-type CGL is decreased.

In addition, when an alkali metal is doped into the N-type CGL, the alkali metal may be diffused into the P-type CGL such that the lifetime of the OLED is reduced.

SUMMARY OF THE INVENTION

Accordingly, the present invention is directed to an organic compound and an organic light emitting diode and an organic light emitting display (OLED) device including the same that substantially obviate one or more of the problems due to limitations and disadvantages of the related art.

An object of the present invention is to provide an organic compound being capable of preventing the decrease of an electron injection property and the lifetime.

An object of the present invention is to provide an organic light emitting diode and an OLED device having improved electron injection property and lifetime.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described herein, an organic compound is represented by following Formula:

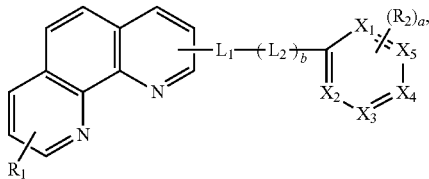

wherein each of $X_1$ to $X_5$ is independently selected from a carbon atom (C) or a nitrogen atom (N), and at least two or three of $X_1$ to $X_5$ are N, wherein each of $R_1$ and $R_2$ is independently selected from a substituted or non-substituted aryl group or a substituted or non-substituted heteroaryl group, and "a" is an integer between zero (0) to 3, and wherein each of $L_1$ and $L_2$ is independently selected from a substituted or non-substituted arylene group or a substituted or non-substituted heteroarylene group, and "b" is zero (0) or 1.

In another aspect, an organic light emitting diode comprises first and second electrodes facing each other; a first emitting part between the first and second electrodes and including a first emitting material layer and an electron transporting layer; a second emitting part between the first emitting part and the second electrode and including a second emitting material layer; and a charge generation layer between the first and second emitting parts, wherein at least one of the electron transporting layer and the charge generation layer includes an organic compound represented by following Formula:

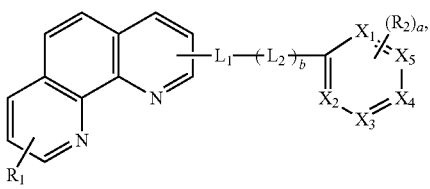

wherein each of $X_1$ to $X_5$ is independently selected from a carbon atom (C) or a nitrogen atom (N), and at least two or three of $X_1$ to $X_5$ are N, wherein each of $R_1$ and $R_2$ is independently selected from a substituted or non-substituted aryl group or a substituted or non-substituted heteroaryl group, and "a" is an integer between zero (0) to 3, and wherein each of $L_1$ and $L_2$ is independently selected from a substituted or non-substituted arylene group or a substituted or non-substituted heteroarylene group, and "b" is zero (0) or 1.

In another aspect, an organic light emitting display device comprises a substrate; an organic light emitting diode over the substrate and including first and second electrodes facing each other, a first emitting part between the first and second electrodes and including a first emitting material layer and an electron transporting layer, a second emitting part between the first emitting part and the second electrode and including a second emitting material layer and a charge generation layer between the first and second emitting parts; and a thin film transistor between the substrate and the organic light emitting diode and connected to the first electrode, wherein at least one of the electron transporting layer and the charge generation layer includes an organic compound represented by following Formula:

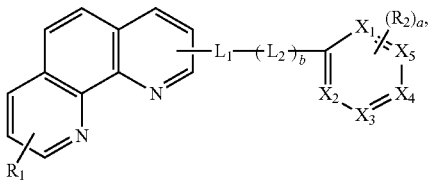

wherein each of $X_1$ to $X_5$ is independently selected from a carbon atom (C) or a nitrogen atom (N), and at least two or three of $X_1$ to $X_5$ are N, wherein each of $R_1$ and $R_2$ is independently selected from a substituted or non-substituted aryl group or a substituted or non-substituted heteroaryl group, and "a" is an integer between zero (0) to 3, and wherein each of $L_1$ and $L_2$ is independently selected from a substituted or non-substituted arylene group or a substituted or non-substituted heteroarylene group, and "b" is zero (0) or 1.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. The patent or application file contains at least one color drawing. Copies of this patent or patent application publication with color drawing will be provided by the USPTO upon request and payment of the necessary fee.

FIGS. 4A to 4C are graphs showing emitting properties of an organic light emitting diode including an organic compound in an N-type CGL.

DETAILED DESCRIPTION OF THE PREFERRED EMBODIMENTS

Reference will now be made in detail to the preferred embodiments, examples of which are illustrated in the accompanying drawings.

Figure 1:
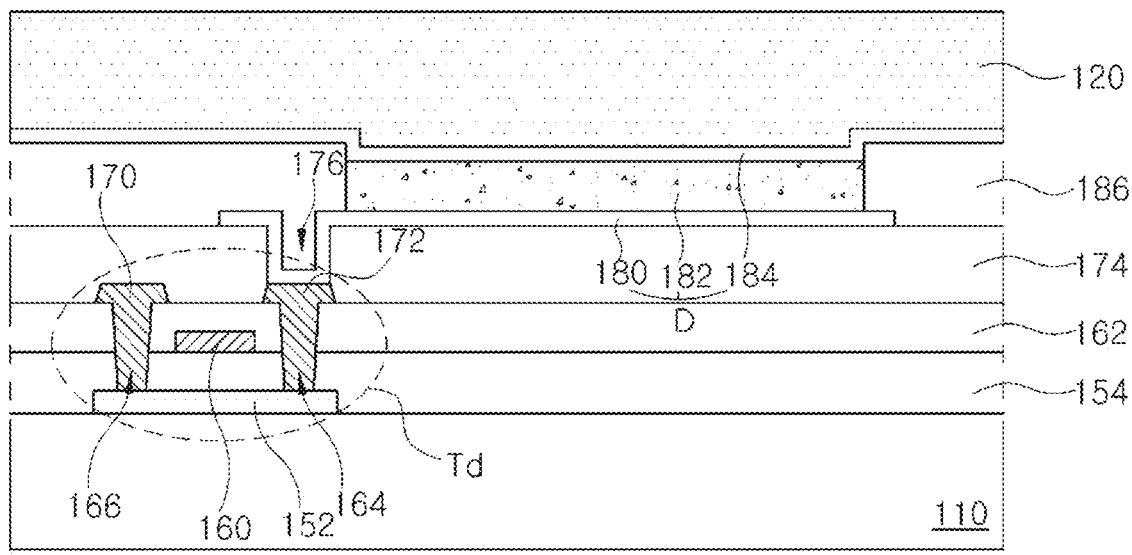
FIG. 1 is a schematic cross-sectional view of an OLED device according to an embodiment of the present invention.

FIG. 1 is a schematic cross-sectional view of an OLED device according to an embodiment of the present invention. All components of the OLED device according to all embodiments of the present invention are operatively coupled and configured.

As shown in FIG. 1, an OLED device 100 includes a substrate 110, an organic light emitting diode D over the substrate 110, an encapsulation film 120 covering the organic light emitting diode D.

A driving thin film transistor (TFT) Td is disposed on the substrate 110, and the organic light emitting diode D is connected to the driving TFT Td.

A gate line and a data line are disposed on or over the substrate 110 and cross each other to define a pixel region. In addition, a power line, which is parallel to and spaced apart from the gate line or the data line, a switching TFT, which is electrically connected to the gate line and the data line, and a storage capacitor, which is connected to the power line and an electrode of the switching TFT may be formed on or over the substrate 110.

The driving TFT Td is connected to the switching TFT and includes a semiconductor layer 152, a gate electrode 160, a source electrode 170 and a drain electrode 172.

The semiconductor layer 152 is formed on the substrate 110. The semiconductor layer 152 may be formed of an oxide semiconductor material or a poly-silicon.

When the semiconductor layer 152 includes the oxide semiconductor material, a light-shielding pattern may be formed under the semiconductor layer 152. The light to the semiconductor layer 152 is shielded or blocked by the light-shielding pattern such that thermal degradation of the semiconductor layer 152 can be prevented. On the other hand, when the semiconductor layer 152 includes polycrystalline silicon, impurities may be doped into both sides of the semiconductor layer 152.

A gate insulating layer 154 is formed on the semiconductor layer 152. The gate insulating layer 154 may be formed of an inorganic insulating material such as silicon oxide or silicon nitride.

The gate electrode 160, which is formed of a conductive material, e.g., metal, is formed on the gate insulating layer 154 to correspond to a center of the semiconductor layer 152. The gate electrode 160 is connected to the switching TFT.

An interlayer insulating layer 162, which is formed of an insulating material, is formed on an entire surface of the substrate 110 including the gate electrode 160. The interlayer insulating layer 162 may be formed of an inorganic insulating material, e.g., silicon oxide or silicon nitride, or an organic insulating material, e.g., benzocyclobutene or photo-acryl.

The interlayer insulating layer 162 includes first and second contact holes 164 and 166 exposing both sides of the semiconductor layer 152. The first and second contact holes 164 and 166 are positioned at both sides of the gate electrode 160 to be spaced apart from the gate electrode 160.

The source electrode 170 and the drain electrode 172, which are formed of a conductive material, e.g., metal, are formed on the interlayer insulating layer 162. The source electrode 170 and the drain electrode 172 are spaced apart from each other with respect to the gate electrode 160 and respectively contact both sides of the semiconductor layer 152 through the first and second contact holes 164 and 166.

In the driving TFT Td, the gate electrode 160, the source electrode 170 and the drain electrode 172 are positioned over the semiconductor layer 152. Namely, the driving TFT Td has a coplanar structure.

Alternatively, in the driving TFT Td, the gate electrode may be positioned under the semiconductor layer, and the source and drain electrodes may be positioned over the semiconductor layer such that the driving TFT Td may have an inverted staggered structure. In this instance, the semiconductor layer may include amorphous silicon.

The switching TFT may have substantially the same structure as the driving TFT Td.

A passivation layer 174, which includes a drain contact hole 176 exposing the drain electrode 172 of the driving TFT Td, is formed to cover the driving TFT Td.

A first electrode 180, which is connected to the drain electrode 172 of the driving TFT Td through the drain contact hole 176, is separately formed on the passivation layer 174 in each pixel region.

The first electrode 180 may be an anode and may be formed of a conductive material having a relatively high work function. For example, the first electrode 180 may be formed of a transparent conductive material, such as indium-tin-oxide (ITO), indium-zinc-oxide (IZO) or zinc oxide (ZnO).

When the OLED device 100 of the present invention is a top-emission type, a reflection electrode or a reflection layer may be formed under the first electrode 180. For example, the reflection electrode or the reflection layer may be formed of aluminum (Al), silver (Ag), nickel (Ni) or aluminum-palladium-copper (APC) alloy.

A bank layer 186, which covers edges of the first electrode 180, is formed on the passivation layer 174. The bank 186 exposes a center of the first electrode 180 in the pixel region.

An organic emitting layer 182 is formed on the first electrode 180. As explained below, the organic emitting layer includes at least two emitting parts such that the organic light emitting diode D has a tandem structure. The emitting parts are vertically stacked.

A second electrode 184 is formed over the substrate 110 including the emitting layer 182. The second electrode 184 is positioned at an entire surface of the display area. The second electrode 184 may be a cathode and may be formed of a conductive material having a relatively low work function. For example, the second electrode 184 may be formed of aluminum (Al), magnesium (Mg) or Al—Mg alloy.

The first electrode 180, the emitting layer 182 and the second electrode 184 constitute the organic light emitting diode D.

The encapsulation film 120 is formed on the organic light emitting diode D to prevent penetration of moisture into the organic light emitting diode D. For example, the encapsulation film 120 may has a triple-layered structure of a first inorganic layer, an organic layer and a second inorganic layer. However, it is not limited thereto.

Figure 2A:
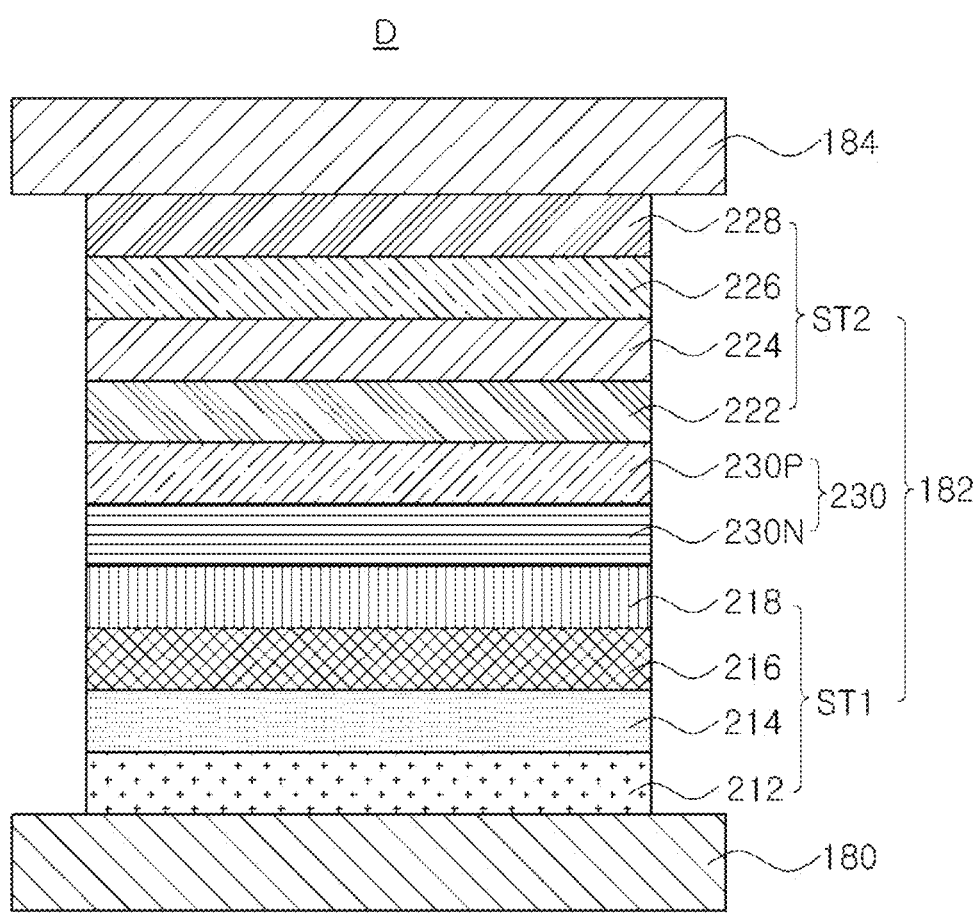
FIGS. 2A and 2B are schematic cross-sectional views of an organic light emitting diode according to an embodiment of the present invention, respectively.
Figure 2B:
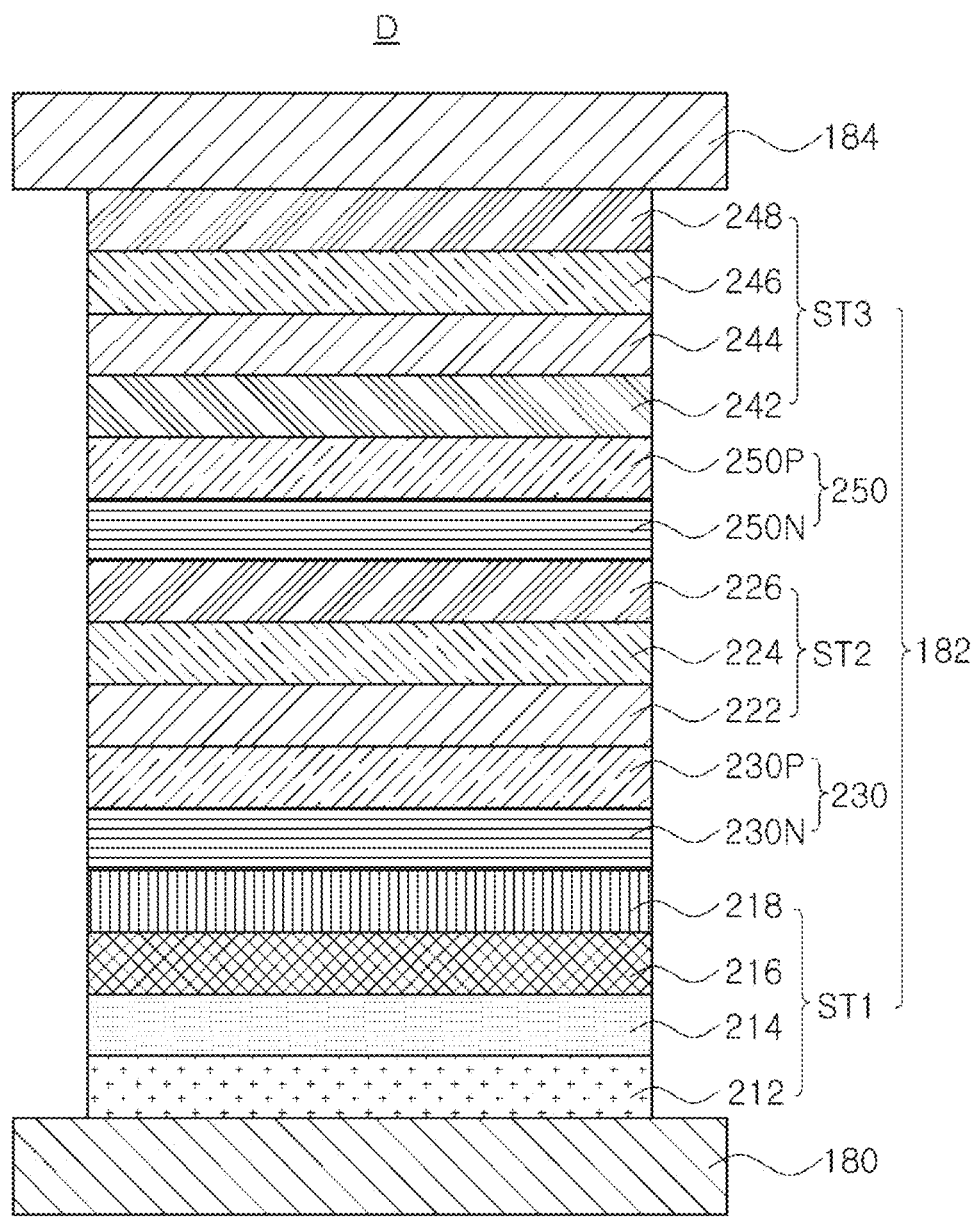

FIGS. 2A and 2B are schematic cross-sectional views of an organic light emitting diode according to an embodiment of the present invention, respectively.

As shown in FIG. 2A, the organic light emitting diode D includes a first electrode 180, a second electrode 184, an organic emitting layer 182 between the first and second electrodes 180 and 184 and including first and second emitting parts ST1 and ST2 and a charge generation layer (CGL) 230.

As mentioned above, the first electrode 180 is the anode for injecting a hole and includes a high work function conductive material, e.g., ITO, IZO or ZO. The second electrode 184 is the cathode for injecting an electron and includes a low work function conductive material, e.g., Al, Mg or Al—Mg alloy.

The CGL 230 is positioned between the first and second emitting parts ST1 and ST2. Namely, the first emitting part ST1, the CGL 230 and the second emitting part ST2 are sequentially stacked on the first electrode 180. In other words, the first emitting part ST1 is positioned between the first electrode 180 and the CGL 230, and the second emitting part ST2 is positioned between the second electrode 184 and the CGL 230.

The first emitting part ST1 may include a hole injection layer (HIL) 212, a first hole transporting layer (HTL) 214, a first emitting material layer (EML) 216 and a first electron transporting layer (ETL) 218 sequentially stacked on the first electrode 180. Namely, the HIL 212 and the first HTL 214 are positioned between the first electrode 180 and the first EML 216, and the HIL 212 is positioned between the first electrode 180 and the first HTL 214. In addition, the first ETL 218 is positioned between the first EML 216 and the CGL 230.

A hole injection from the first electrode 180 into the first EML 216 is improved by the HIL 212. The HIL 212 may include at least one selected from the group consisting of copper phthalocyanine (CuPC), poly(3,4)-ethylenedioxythiophene (PEDOT) and polyaniline, but it is not limited thereto.

The HIL 212 may have a thickness of about 1 to 150 nm. The hole injection property may be improved with a thickness above 1 nm, and an increase of the driving voltage resulting from an increase of a thickness of the HIL 212 may be prevented with a thickness below 150 nm. The HIL 212 may be omitted according to the structure or property of the organic light emitting diode.

A hole transporting is improved by the first HTL 214. The first HTL 214 may include at least one selected from the group consisting of N,N'-bis(naphthalen-1-yl)-N,N'-bis(phenyl)-2,2'-dimethylbenzidine (NPD), N,N'-bis-(3-methylphenyl)-N,N'-bi s-(phenyl)-benzidine (TPD), 2,2',7,7'-tetrakis(N,N-diphenylamino)-9,9'-spirofluorene (spiro-TAD) and 4,4',4''-Tris(N-3-methylphenyl-N-phenylamino)-triphenylamine (MTDATA), but it is not limited thereto.

The first HTL 214 may have a thickness of about 1 to 150 nm. The hole transporting property may be improved with a thickness above 1 nm, and an increase of the driving voltage resulting from an increase of a thickness of the first HTL 214 may be prevented with a thickness below 150 nm.

The first EML 216 may be a blue EML. Alternatively, the first EML 216 may be a red EML, a green EML or a yellow EML. When the first EML 216 is the blue EML, the first EML 216 may be a dark blue EML or a sky blue EML. In addition, the first EML 216 may be a double-layered structure of the blue EML and the red EML, the blue EML and yellow-green EML, or the blue EML and the green EML.

When the first EML 216 is the red EML, the first EML 216 may be a phosphorescent EML including a host, e.g., 4,4'-bis(carbazol-9-yl)biphenyl (CBP), and at least one dopant selected from the group consisting of bis(1-phenylisoquinoline)acetylacetonate iridium (PIQIr(acac), bis(1-phenylquinoline)acetylacetonate iridium(PQIr(acac), tris(1-phenylquinoline)iridium(PQIr) and octaethylporphyrin platinum (PtOEP), but it is not limited thereto. Alternatively, the first EML 216 may be a fluorescent EML including PBD:Eu(DBM)3(Phen) or perylene. In this instance, the first emitting part ST1 has an emission peak range of about 600 to 650 nm.

When the first EML 216 is the green EML, the first EML 216 may be a phosphorescent EML including a host, e.g., CBP, and a dopant of iridium complex, but it is not limited thereto. Alternatively, the first EML 216 may a fluorescent EML including tris(8-hydroxyquinolinato)aluminum (Alq3). In this instance, the first emitting part ST1 has an emission peak range of about 510 to 570 nm.

When the first EML 216 is the blue EML, the first EML 216 may be a phosphorescent EML including a host, e.g., CBP, and a dopant of iridium complex, but it is not limited thereto. Alternatively, the first EML 216 may a fluorescent EML including spiro-DPVBi, Spiro-CBP, distyryl benzene (DSB), distyryl arene (DSA), PFO-based polymer or PPV-based polymer. As mentioned above, the first EML 216 may be a sky blue EML or deep blue (dark blue) EML. In this instance, the first emitting part ST1 has an emission peak range of about 440 to 480 nm.

On the other hand, to improve the emitting efficiency (red efficiency), the first emitting part ST1 may include two EMLs. For example, the first emitting part ST1 may include the blue EML and the red EML. In this instance, the first emitting part ST1 has an emission peak range of about 440 to 650 nm.

In addition, the first EML 216 may have a single-layered structure of the yellow-green EML or a double-layered structure of the yellow-green EML and the green EML. In this instance, the first EML 216 may include at least one host selected from the group consisting of CBP and bis(2-methyl-8-quinolinolate)-4-(phenylphenolato)aluminium (BAlq) and a phosphorescent yellow-green dopant. The first emitting part ST1 has an emission peak range of about 510 to 590 nm.

When the first emitting part ST1 includes two EMLs of the yellow-green EML and the red EML to improve the emitting efficiency (red efficiency), the first emitting part ST1 has an emission peak range of about 510 to 650 nm.

An electron transporting is improved by the first ETL 218. The first ETL 218 may include an organic compound represented by Formula 1, tris(8-hydroxy-quinolinato)aluminum (Alq3), 2-(4-biphenyl)-5-(4-tertbutylphenyl)-1,3,4-oxadiazole (PBD), 3-(4-biphenyl)-4-phenyl-5-tertbutylphenyl-1,2,4-triazole (TAZ) or Bis(2-methyl-8-quinolinolate)-4-(phenylphenolato)aluminum (BAlq), but it is not limited thereto.

The first ETL 218 may have a thickness of about 1 to 150 nm. The electron transporting property may be improved with a thickness above 1 nm, and an increase of the driving voltage resulting from an increase of a thickness of the first ETL 218 may be prevented with a thickness below 150 nm.

The second emitting part ST2 may include a second HTL 222, a second EML 224, a second ETL 226 and an electron injection layer (EIL) 228. The second HTL 222 is positioned between the CGL 230 and the second EML 224, and the second ETL 226 is positioned between the second EML 224 and the second electrode 184. In addition, the EIL 228 is positioned between the second ETL 226 and the second electrode 184.

The second HTL 222 and the second ETL 226 may be the same as or different from the first HTL 214 and the first ETL 218 in the first emitting part ST1, respectively. The EIL 228 may be omitted according to the structure or property of the organic light emitting diode.

The second EML 224 may be red, green, blue or yellow-green EML. For example, when the first EML 216 is the blue EML, the second EML 224 may be yellow-green EML. Alternatively, the first EML 216 may be the yellow-green EML, and the second EML 224 may be the blue EML.

When the second EML 224 is the yellow-green EML, the second EML 224 may have a single-layered structure of the yellow-green EML or a double-layered structure of the yellow-green EML and the green EML. For example, the single-layered second EML 224 may include at least one host selected from the group consisting of CBP and bis(2-methyl-8-quinolinolate)-4-(phenylphenolato)aluminium (BAlq) and a phosphorescent yellow-green dopant, but it is not limited thereto.

An electron injection is improved by the EIL 228. The EIL 228 may include at least one selected from the group consisting of tris(8-hydroxy-quinolinato)aluminum (Alq3), 2-(4-biphenyl)-5-(4-tertbutylphenyl)-1,3,4-oxadiazole (PBD), 3-(4-biphenyl)-4-phenyl-5-tertbutylphenyl-1,2,4-triazole TAZ) and Bis(2-methyl-8-quinolinolate)-4-(phenylphenolato)aluminum (BAlq), but it is not limited thereto.

On the other hand, the EIL 228 may further include a metal compound. For example, the metal compound may be at least one selected from the group consisting of LiF, NaF, KF, RbF, CsF, FrF, BeF2, MgF2, CaF2, SrF2, BaF2 and RaF2, but it is not limited thereto.

The EIL 228 may have a thickness of about 1 to 50 nm. The electron injection property may be improved with a thickness above 1 nm, and an increase of the driving voltage resulting from an increase of a thickness of the EIL 228 may be prevented with a thickness below 50 nm.

The CGL 230 is positioned between the first emitting part ST1 and the second emitting part ST2. Namely, the first and second emitting parts ST1 and ST2 are connected by the CGL 230. The CGL 230 may be a P-N junction type CGL including an N-type CGL 230N and a P-type CGL 230P.

The N-type CGL 230N is positioned between the first ETL 218 and the second HTL 222, and the P-type CGL 230P is positioned between the N-type CGL 230N and the second HTL 222.

The CGL 230 generates a charge or separates a charge into a hole and an electron such that the hole and the electron are provided into the first and second emitting parts ST1 and ST2.

The N-type CGL 230N provides the electron into the first ETL 218 of the first emitting part ST1, and the first ETL 218 provide the electron into the first EML 216 of the first emitting part ST1. On the other hand, the P-type CGL 230P provide the hole into the second HTL 222 of the second emitting part ST2, and the second HTL 222 provide the hole into the second EML 224 of the second emitting part ST2. Accordingly, the emitting efficiency of the organic light emitting diode D including a plurality of EMLs or a plurality of emitting parts is improved, and the driving voltage of the organic light emitting diode D is reduced.

Referring to FIG. 2B, an organic light emitting diode D includes a first electrode 180, a second electrode 184, an organic emitting layer 182 between the first and second electrodes 180 and 184 and including first to third emitting parts ST1, ST2 and ST3 and first and second charge generation layers (CGLs) 230 and 250. Alternatively, four or more emitting parts and three or more CGLs may be disposed between the first and second electrodes 180 and 184.

As mentioned above, the first electrode 180 is the anode for injecting a hole and includes a high work function conductive material, e.g., ITO, IZO or ZO. The second electrode 184 is the cathode for injecting an electron and includes a low work function conductive material, e.g., Al, Mg or Al—Mg alloy.

The first and second CGLs 230 and 250 are positioned between the first and second emitting parts ST1 and ST2 and the second and third emitting parts ST2 and ST3, respectively. Namely, the first emitting part ST1, the first CGL 230, the second emitting part ST2, the second CGL 250 and the third emitting part ST3 are sequentially stacked on the first electrode 180. In other words, the first emitting part ST1 is positioned between the first electrode 180 and the first CGL 230, and the second emitting part ST2 is positioned between the First and Second CGLs 230 and 250. In addition, the third emitting part ST3 is positioned between the second electrode 184 and the second CGL 250.

The first emitting part ST1 may include an HIL 212, a first HTL 214, a first EML 216 and a first ETL 218 sequentially stacked on the first electrode 180. Namely, the HIL 212 and the first HTL 214 are positioned between the first electrode 180 and the first EML 216, and the HIL 212 is positioned between the first electrode 180 and the first HTL 214. In addition, the first ETL 218 is positioned between the first EML 216 and the first CGL 230.

The HIL 212, the first HTL 214, the first EML 216 and the first ETL 218 may have substantially the same property and structure as those in FIG. 2A. For example, the first EML 216 may be a blue EML such that the first emitting part ST1 may have an emission peak range of about 440 to 480 nm.

The second emitting part ST2 may include a second HTL 222, a second EML 224 and a second ETL 226. The second HTL 222 is positioned between the first CGL 230 and the second EML 224, and the second ETL 226 is positioned between the second EML 224 and the second CGL 250.

The second HTL 222, second EML 224 and the second ETL 226 may have substantially the same property and structure as those in FIG. 2A. For example, the second EML 224 may be a yellow-green EML such that the second emitting part ST2 may have an emission peak range of about 510 to 590 nm.

The third emitting part ST3 may include a third HTL 242, a third EML 244, a third ETL 246 and an EIL 248. The third HTL 242 is positioned between the second CGL 250 and the third EML 244, and the third ETL 246 is positioned between the third EML 244 and the second electrode 184. In addition, the EIL 248 is positioned between the third ETL 246 and the second electrode 184.

The third HTL 242, the third ETL 246 and the EIL 248 may have substantially the same property and structure as the second HTL 222, the second ETL 226 and the EIL 228 in FIG. 2A.

The first CGL 230 is positioned between the first emitting part ST1 and the second emitting part ST2, and the second CGL 250 is positioned between the second emitting part ST2 and the third emitting part ST3. Each of the first and second CGLs 230 and 250 may be a P-N junction type CGL. The first CGL 230 includes an N-type CGL 230N and a P-type CGL 230P, and the second CGL 250 includes an N-type CGL 250N and a P-type CGL 250P.

In the first CGL 230, the N-type CGL 230N is positioned between the first ETL 218 and the second HTL 222, and the P-type CGL 230P is positioned between the N-type CGL 230N and the second HTL 222.

In the second CGL 250, the N-type CGL 250N is positioned between the second ETL 226 and the third HTL 242, and the P-type CGL 250P is positioned between the N-type CGL 250N and the third HTL 242.

Each of the first and second CGLs 230 and 250 generates a charge or separates a charge into a hole and an electron such that the hole and the electron are provided into the first to third emitting parts ST1 to ST3.

Namely, in the first CGL 230, the N-type CGL 230N provides the electron into the first ETL 218 of the first emitting part ST1, and the P-type CGL 230P provide the hole into the second HTL 222 of the second emitting part ST2. In addition, in the second CGL 250, the N-type CGL 250N provides the electron into the second ETL 226 of the second emitting part ST2, and the P-type CGL 250P provide the hole into the third HTL 242 of the third emitting part ST3. Accordingly, the emitting efficiency of the organic light emitting diode D including a plurality of EMLs or a plurality of emitting parts is improved, and the driving voltage of the organic light emitting diode D is reduced.

However, when the electrons are transported from the N-type CGLs 230N and 250N into the first and second ETLs 218 and 226, the driving voltage is increased because of a lowest unoccupied molecular orbital (LUMO) energy level difference between each of the first and second ETLs 218 and 226 and each of the N-type CGLs 230N and 250N.

To overcome the above problem, at least one of the first and second ETLs 218 and 226 and the N-type CGLs 230N and 250N includes an organic compound represented in Formula 1. In addition, each of the N-type CGLs 230N and 250N may further include alkali metal or alkali earth metal.

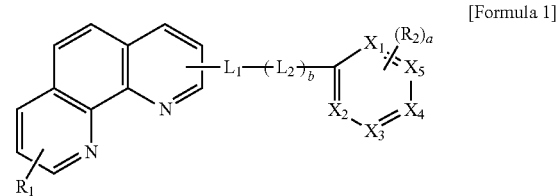

[Formula 1]

As shown in Formula 1, the organic compound of the present invention includes a phenanthroline core. Due to the phenanthroline core, an electron transporting property of the organic compound is improved. In addition, a diffusion problem of the alkali metal or the alkali earth metal from the N-type CGL into the P-type CGL is prevented.

In Formula 1, each of $X_1$ to $X_5$ is independently selected from a carbon atom (C) or a nitrogen atom (N), and at least two or three of $X_1$ to $X_5$ are N.

In Formula 1, each of $R_1$ and $R_2$ is independently selected from a substituted or non-substituted aryl group or a substituted or non-substituted heteroaryl group, and "a" is an integer between zero (0) to 3.

Each of R1 and R2 is independently selected from C6 to C60 aryl or C6 to C60 heteroaryl. For example, each of R1 and R2 may be selected from one of phenyl, alkylphenyl, biphenyl, alkylbiphenyl, halophenyl, alkoxyphenyl, haloalkoxyphenyl, cyanophenyl, silylphenyl, naphthyl, alkylnaphthyl, halonaphthyl, cyanonaphthyl, silylnaphthyl, phenylnaphthyl, pyridyl, alkylpyridyl, halopyridyl, cyanopyridyl, alkoxypyridyl, silylpyridyl, phenylpyridyl, pyrimidyl, halopyrimidyl, cyanopyridimyl, alkoxypyrimidyl, phenylpyrimidyl, quinolinyl, isoquinolinyl, phenylquinolinyl, quinoxalinyl, pyrazinyl, quinazolinyl, naphthyridinyl, benzothiophenyl, benzofuranyl, dibenzothiophenyl, arylthiazolyl, dibenzofuranyl, fluorenyl, carbazoyl, imidazolyl, carbolinyl, phenanthrenyl, terphenyl, terpyridinyl, phenylterpyridinyl, triphenylenyl, fluoranthenyl and diazafluorenyl.

As a result, due to a pendant including a nitrogen atom, an electron transporting property of the organic compound is further improved, and a highest occupied molecular orbital (HOMO) energy level and the LUMO energy level of the organic compound are controlled.

In addition, a carrier mobility of the organic compound is controlled by linkers L1 and L2. In Formula 1, each of L1 and L2 is independently selected from a substituted or non-substituted arylene group or a substituted or non-substituted heteroarylene group, and "b" is zero (0) or 1.

Each of L1 and L2 is independently selected from $C_6$ to C60 arylene or C6 to C60 heteroarylene. For example, L1 may be selected from one of phenylene, alkylphenylene, cyanophenylene, naphthylene, alkylnaphthylene, biphenylene, alkylbiphenylene, anthracenylene, pyrenylene, benzothiophenylene, benzofuranylene, dibenzothiophenylene, arylthiazolylene, dibenzofuranylene, fluorenylene and triphenylenylene, and L2 may be one of phenylene and naphthylene.

Namely, since the organic compound of the present invention includes the phenanthroline core having two nitrogen atoms, which have a rich electron property, a layer including the organic compound has high electron mobility such that an electron transporting property of the layer is improved. Accordingly, in the organic light emitting diode including the organic compound in the electron transporting layer, an electron from the N-type CGL into the EML is efficiently transported.

In addition, when the organic compound of the present invention having the nitrogen atom of a relatively electron rich sp2 hybrid orbital is included in the N-type CGL, the nitrogen atom of the organic compound is combined or bound with the alkali metal or the alkali earth metal as a dopant in the N-type CGL to form a gap state. As a result, an electron transporting property from the N-type CGL into the ETL is improved.

Moreover, since the alkali metal or the alkali earth metal is combined with the nitrogen atom in the organic compound, the diffusion of the alkali metal or the alkali earth metal into the P-type CGL is prevented.

Furthermore, the N-type CGL and the HTL include the organic compound such that the LUMO energy level difference between the N-type CGL and the HTL is decreased.

Accordingly, when the organic compound of the present invention is used for the N-type CGL and/or the ETL of the organic light emitting diode, the driving voltage of the organic light emitting diode is reduced and the emitting efficiency and the lifetime of the organic light emitting diode are improved.

The organic compound of the present invention for at least one of the N-type CGLs 230N and 250N and the ETLs 218, 226 and 246 may be one of materials in Formula 2.

[Formula 2]

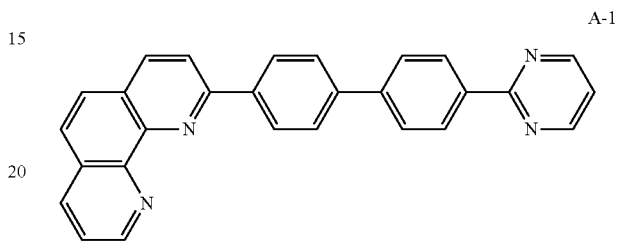

A-1

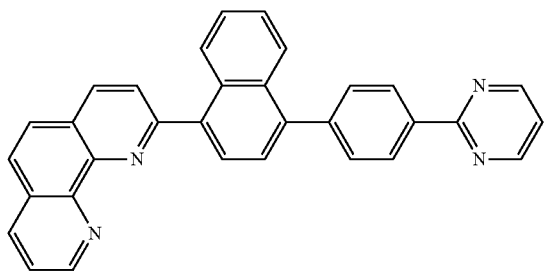

A-2

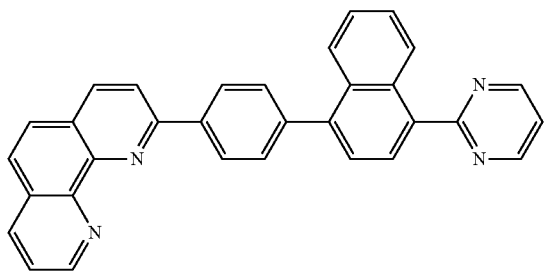

A-3

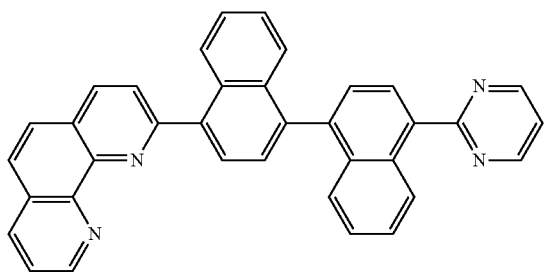

A-4

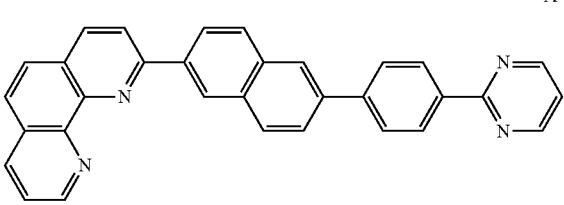

A-5

-continued

A-6

A-7

A-8

A-9

A-10

A-11

A-12

A-13

A-14

A-15

A-16

A-17

A-18
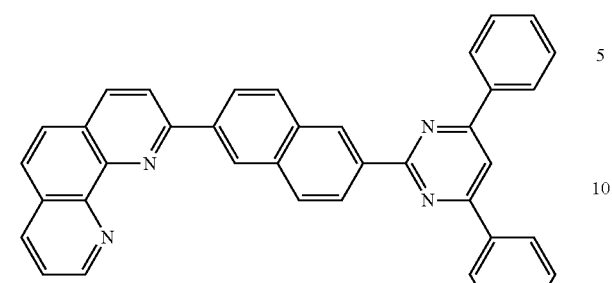
A-19
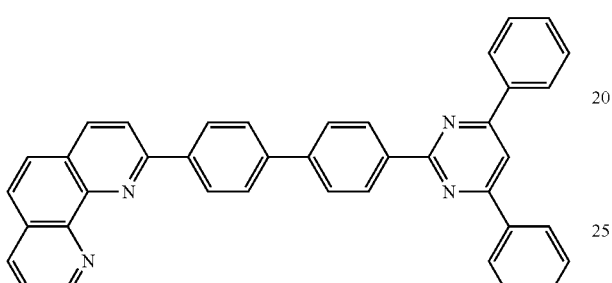
A-20
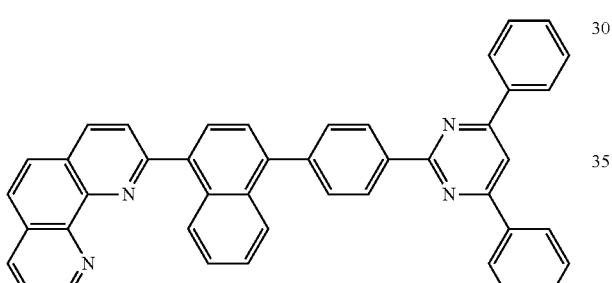
A-21
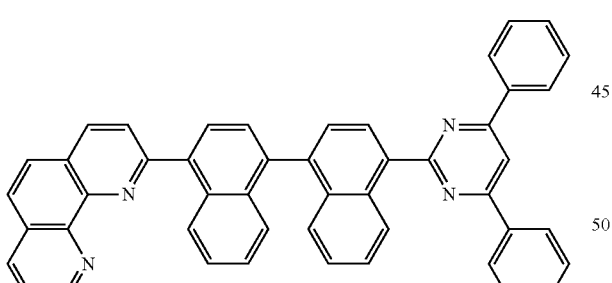
A-22
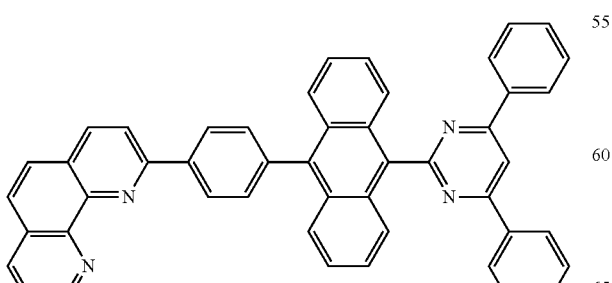
A-23
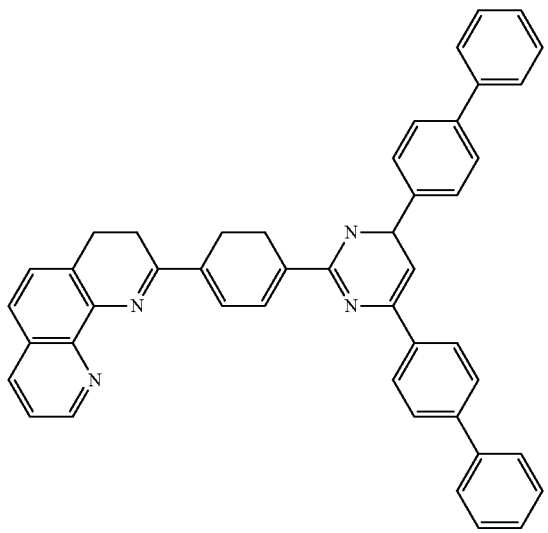
A-24
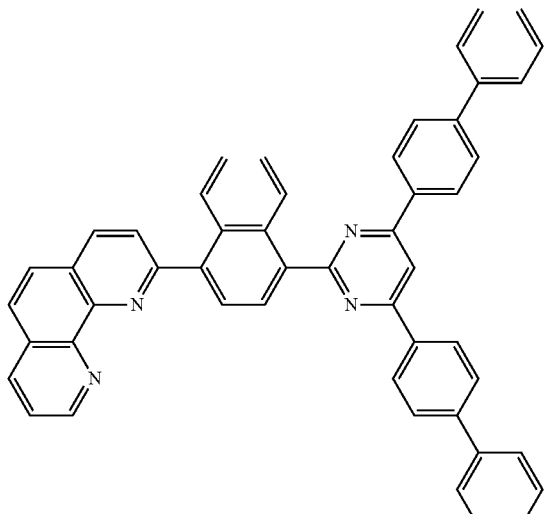
A-25
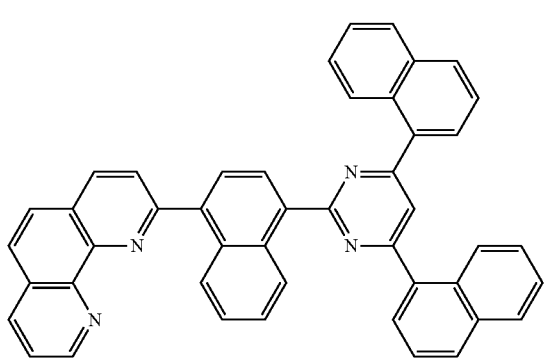

A-26
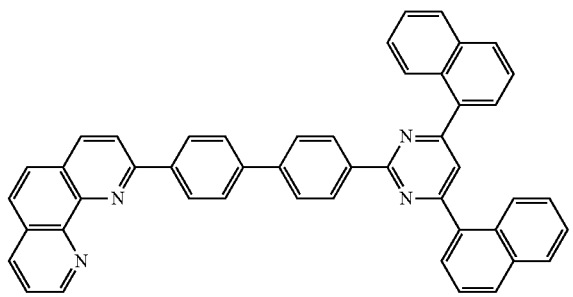
A-27
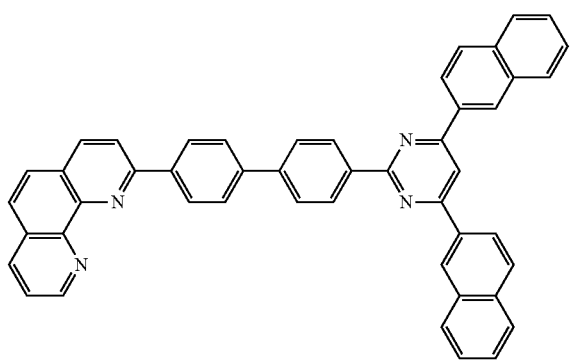
A-28
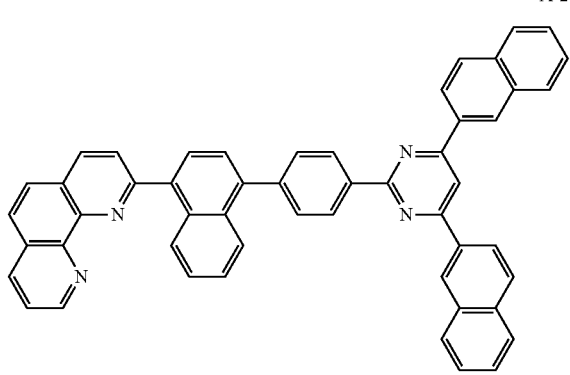
A-29
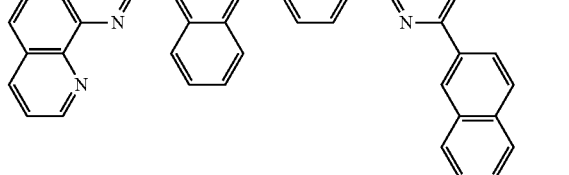
A-30
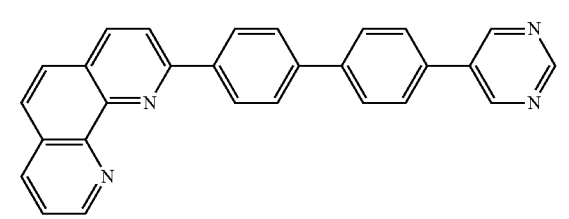
A-31
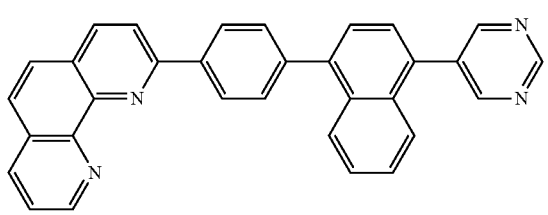
A-32
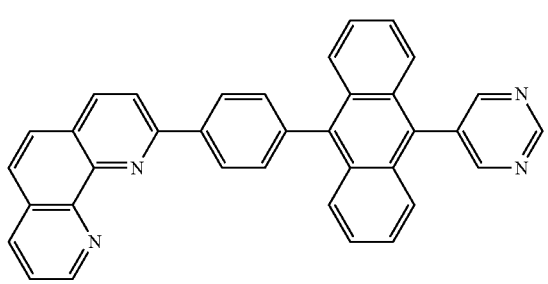
A-33
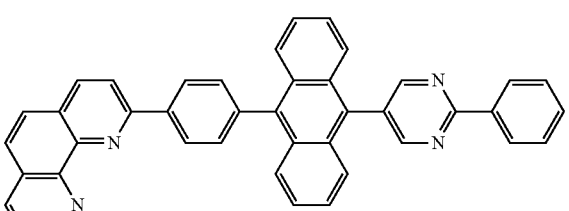
A-34
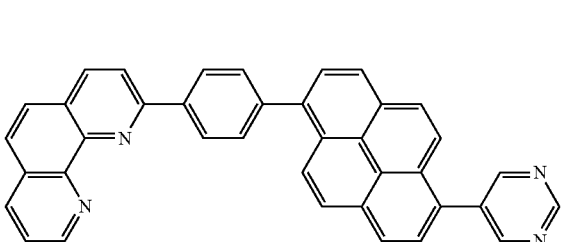
A-35
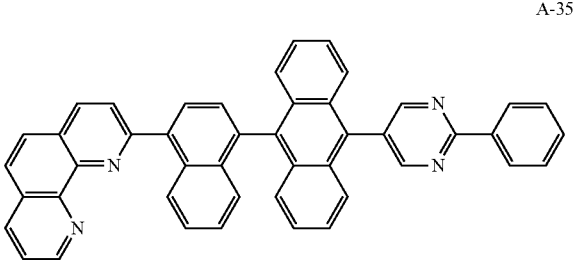
A-36
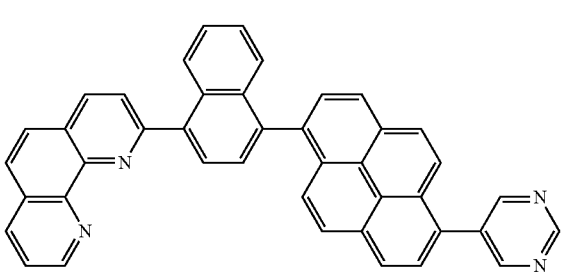

A-37
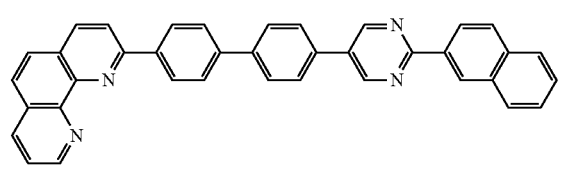
A-38
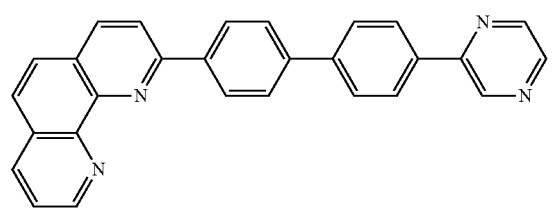
A-39
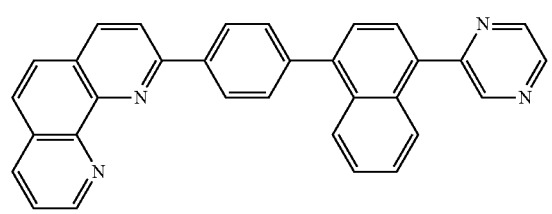
A-40
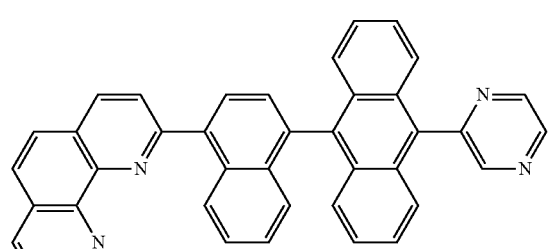
A-41
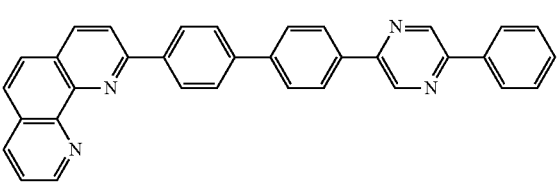
A-42
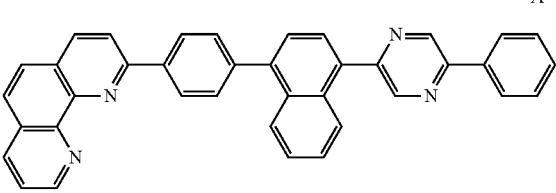
A-43
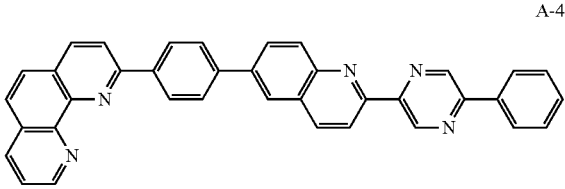
A-44
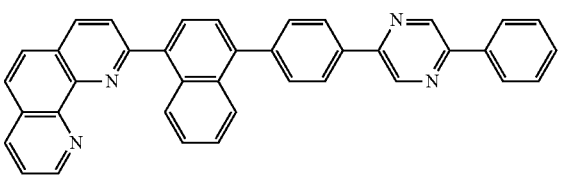
A-45
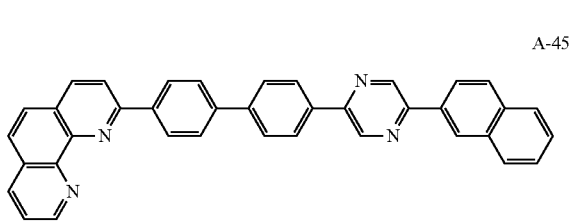
A-46
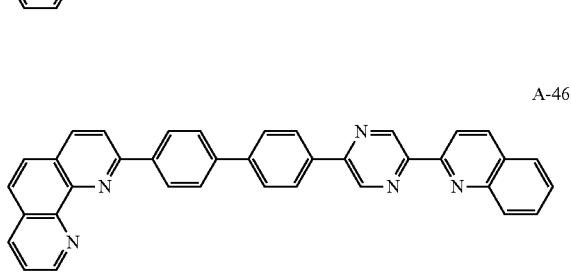
A-47
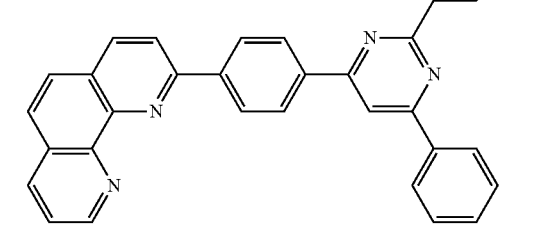
A-48
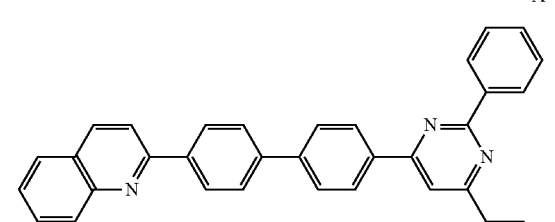
A-49
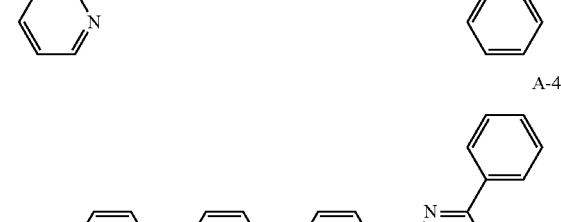

A-50
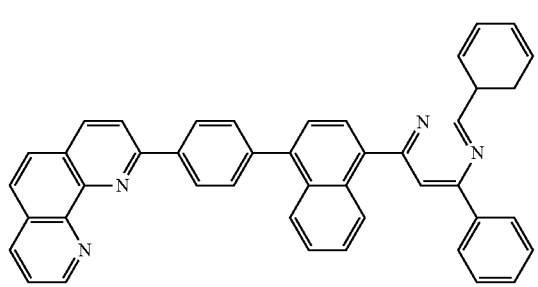
A-51
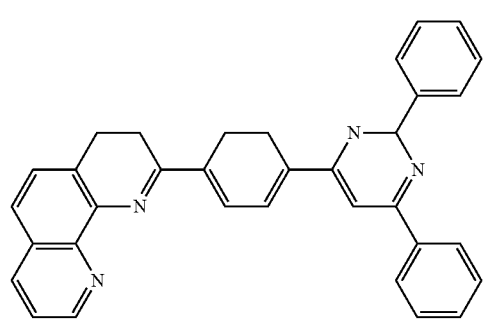
A-52
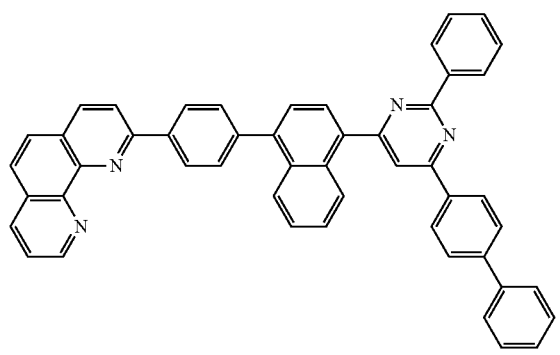
A-53
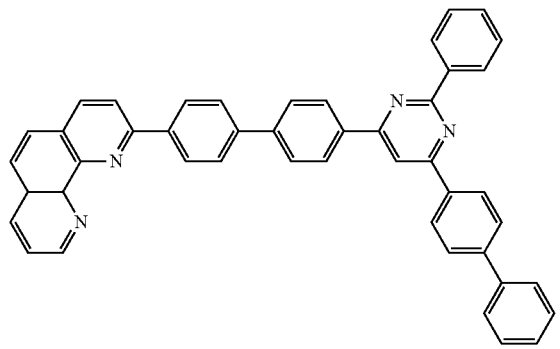
A-54
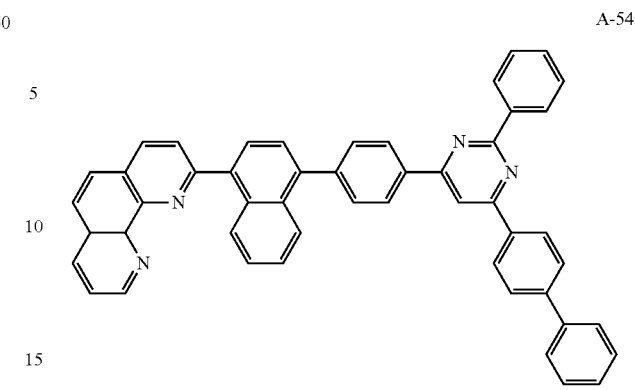
A-55
A-56
A-57

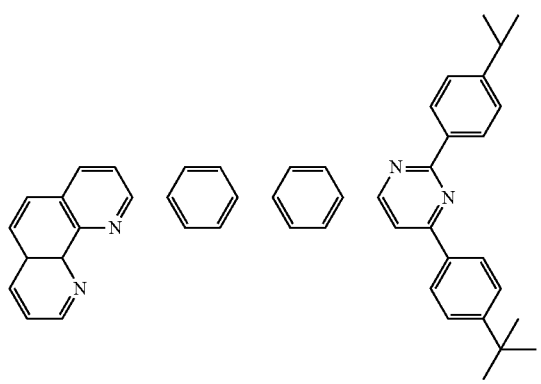
A-58
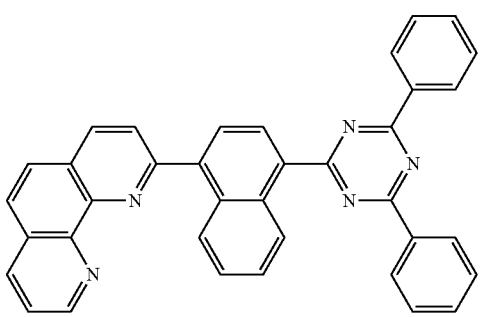
A-62
A-59
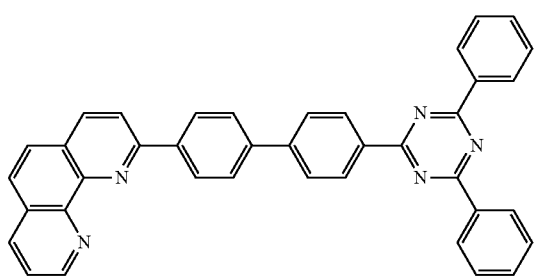
A-63
A-60
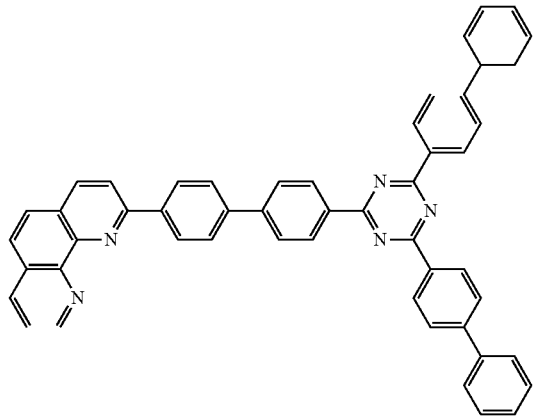
A-64
A-61
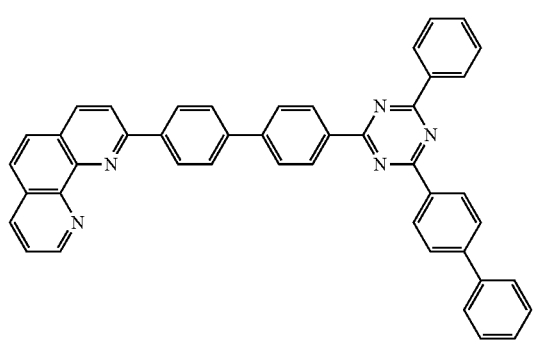
A-65

A-66

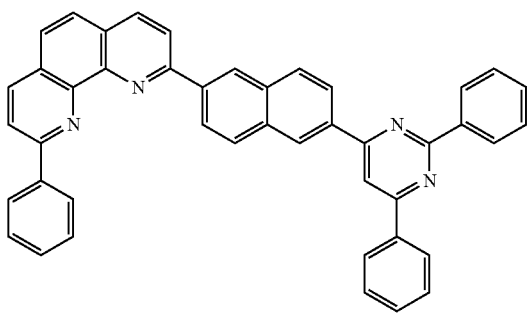

A-67

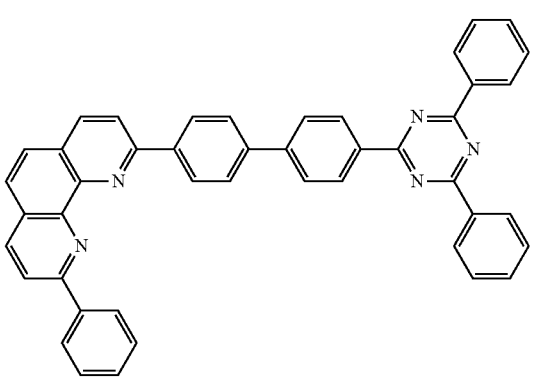

A-68

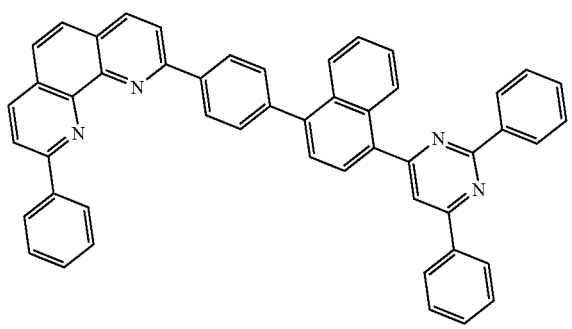

A-69

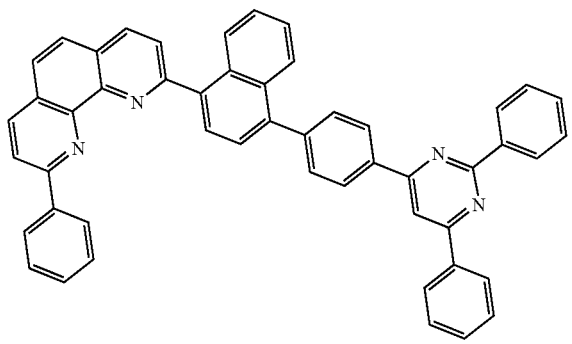

A-70

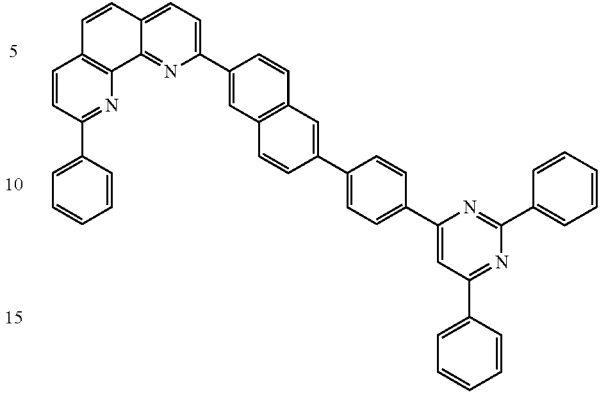

For example, like the compounds A-2, A-4, A-24, A-40, A-49, A-62, and so on, naphthalene may be combined at a 2-position of the phenanthroline core. In this instance, an energy level difference between the N-type CGL and the ETL is reduced such that a tunneling effect for electron transporting is improved or maximized. Namely, in the present invention, the organic compound is included in the N-type CGL and/or the ETL such that the electron transporting property is improved or maximized by the tunneling effect.

In addition, when the organic compound is included in the N-type CGL and/or the ETL, the LUMO energy level difference between the ETL and the N-type CGL is reduced. As a result, the driving voltage increasing problem resulting from the electron transporting from the N-type CGL into the ETL is prevented.

Synthesis
1. Synthesis of Compound A-1
(1) Compound B-1

[Reaction Formula 1-1]

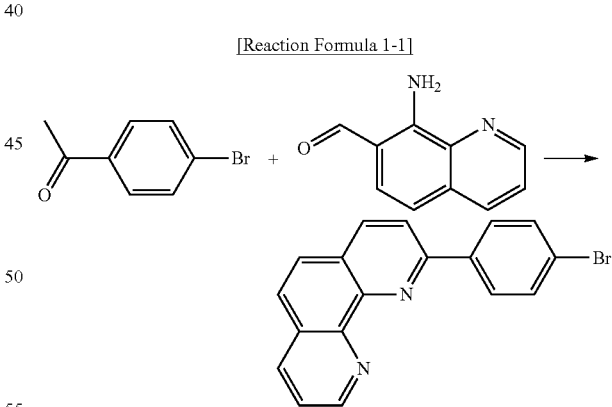

1-(4-bromophenyl)ethanone (15 g, 0.075 mol), 8-aminoquinoline-7-carbaldehyde (13 g, 0.075 mol), absolute ethanol (800 ml) and KOH (15 g) were input into the round bottom flask, and a temperature was increased. The mixture was refluxed and stirred for about 15 minutes. The solution was cooled into the room temperature and extracted by using methylene chloride (MC) and water such that an organic layer is obtained. The organic layer was concentrated under the reduced pressure and re-crystalized by using ethylene acetate such that the compound B-1 (2-(4-bromophenyl)-1,10-phenanthroline, 13.7 g) is obtained.

(2) Compound A-1

[Reaction Formula 1-2]

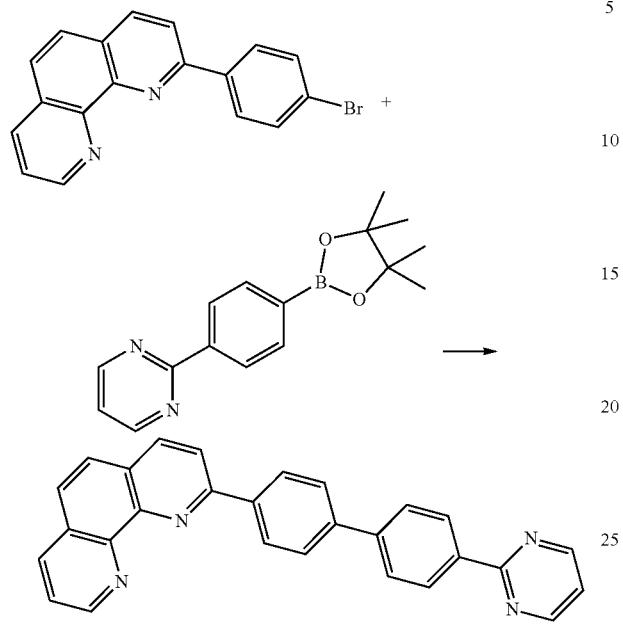

The compound B-1 (10 g, 0.03 mol), 2-(4-(4,4,5,5-tetramethyl-1,3,2-dioxaborolan-2-yl)phenyl)pyrimidine(10.1 g, 0.04 mol), tetrakis(triphenylphosphine)palladium(0) (1.4 g, 0.1 mmol), toluene (200 ml), ethanol (40 ml) and 4M K2CO3 (Potassium carbonate, 15 ml) were refluxed and stirred for about 12 hours in the round bottom flask. After completion of the reaction, the reacting solution was filtered to obtain a crude product. A column separation process using a solvent (CHCl3:MeOH(Methanol)=10:1) is performed to obtain the compound A-1 (5.5 g).

2. Synthesis of Compound A-2
(1) Compound B-2

[Reaction Formula 2-1]

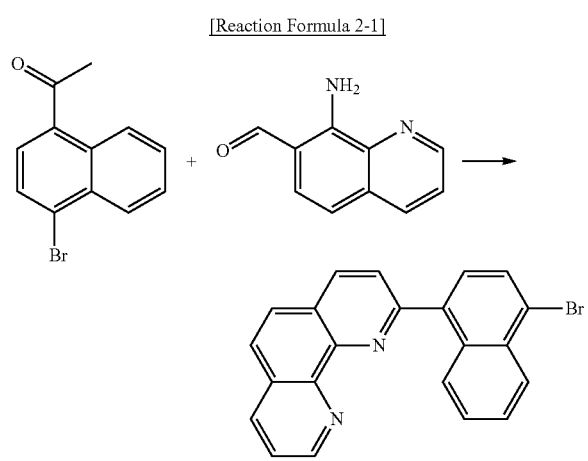

1-(1-bromonaphthalen-4-yl)ethanone (14.5 g, 0.058 mol), 8-aminoquinoline-7-carbaldehyde (10 g, 0.058 mol), absolute ethanol (800 ml) and KOH(potassium hydroxide, 13 g) were input into the round bottom flask, and a temperature was increased. The mixture was refluxed and stirred for about 15 minutes. The solution was cooled into the room temperature and extracted by using methylene chloride (MC) and water such that an organic layer is obtained. The organic layer was concentrated under the reduced pressure and re-crystalized by using ethylene acetate such that the compound B-2 (2-(1-bromonaphthalen-4-yl)-1,10-phenanthroline, 10.5 g) is obtained.

(2) Compound A-2

[Reaction Formula 2-2]

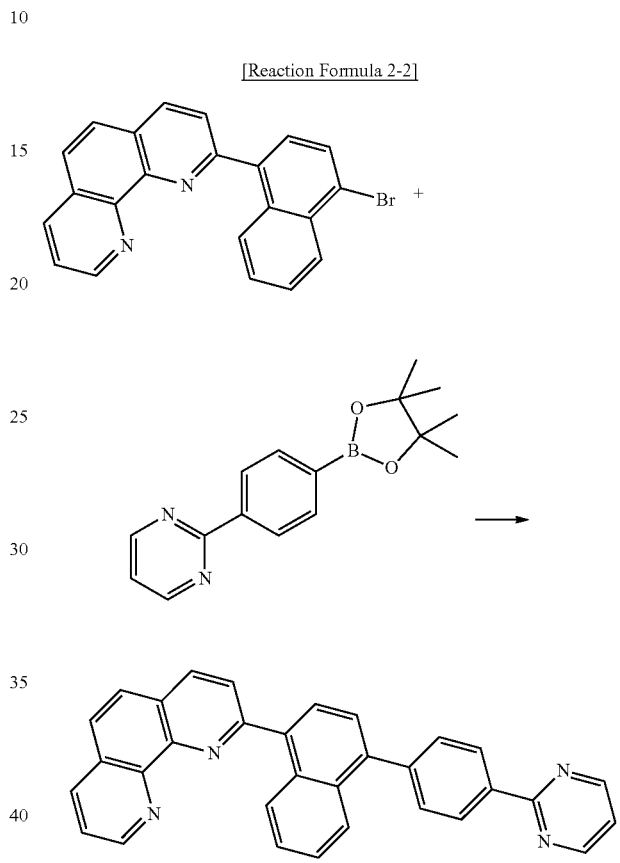

The compound B-2 (10 g, 0.03 mol), 2-(4-(4,4,5,5-tetramethyl-1,3,2-dioxaborolan-2-yl)phenyl)pyrimidine(8.8 g, 0.03 mol), tetrakis(triphenylphosphine)palladium(0) (1.2 g, 0.1 mmol), toluene 200 ml, ethanol (40 ml) and 4M K2CO3 (13 ml) were refluxed and stirred for about 12 hours in the round bottom flask. After completion of the reaction, the reacting solution was filtered to obtain a crude product. A column separation process using a solvent (CHCl3:MeOH=10:1) is performed to obtain the compound A-2 (6.2 g).

3. Synthesis of Compound A-4

[Reaction Formula 3]

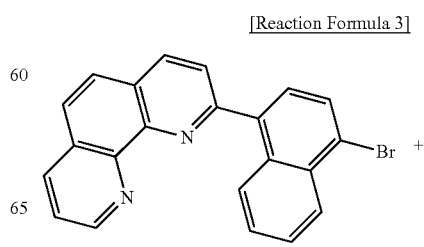

-continued

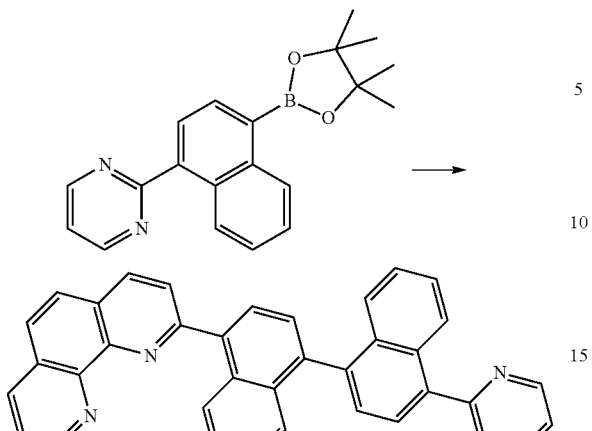

The compound B-2 (10 g, 0.03 mol), 2-(1-(4,4,5,5-tetramethyl-1,3,2-dioxaborolan-2-yl)naphthalen-4-yl)pyrimidine (10.3 g, 0.03 mol), tetrakis(triphenylphosphine)palladium (0) (1.2 g, 0.1 mmol), toluene 200 ml, ethanol (40 ml) and 4M K2CO3 (13 ml) were refluxed and stirred for about 12 hours in the round bottom flask. After completion of the reaction, the reacting solution was filtered to obtain a crude product. A column separation process using a solvent (CHCl3:MeOH=10:1) is performed to obtain the compound A-4 (6.0 g).

4. Synthesis of Compound A-7

(1) Compound B-3

[Reaction Formula 4-1]

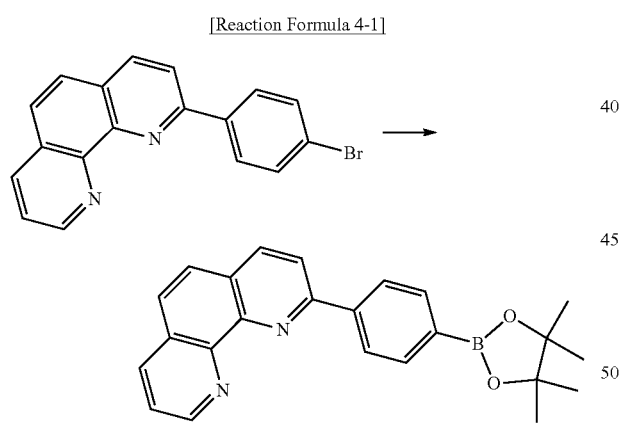

The compound B-2 (10 g, 0.03 mol), bis(pinacolato) diboron (9.1 g, 0.04 mol), [1,1'-bis(diphenylphosphino)ferrocene]dichloropalladium(II) (1.3 g, 0.2 mmol), KOAc(potassium acetate, 10.5 g, 0.11 mol) and 1,4-dioxane (200 ml) were input into the round bottom flask, and a temperature was increased. The mixture was refluxed and stirred for about 12 hours. The solution was cooled into the room temperature and filtered by using celite. Then, the celite was washed by CHCl3. The remaining solution was concentrated under the reduced pressure and re-crystalized by using ethylene acetate such that the compound B-3 (2-(4-(4,4,5, 5-tetramethyl-1,3,2-dioxaborolan-2-yl)phenyl)-1,10-phenanthroline, 8.3 g) is obtained.

(2) Compound A-7

[Reaction Formula 4-2]

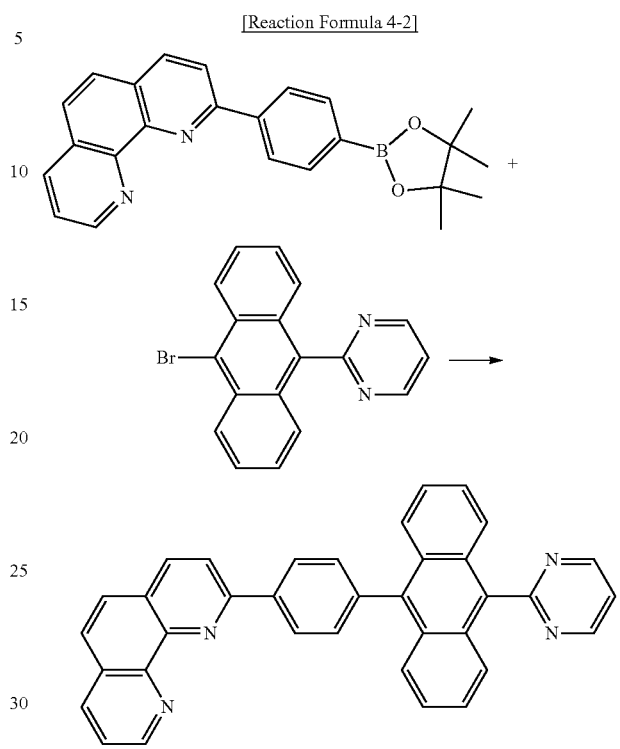

The compound B-3 (5 g, 0.01 mol), 2-(10-bromoanthracen-9-yl)pyrimidine(5.3 g, 0.02 mol), tetrakis(triphenylphosphine)palladium(0) (0.6 g, 0.05 mmol), toluene 100 ml, ethanol (20 ml) and 4M K2CO3 (7 ml) were refluxed and stirred for about 12 hours in the round bottom flask. After completion of the reaction, the reacting solution was filtered to obtain a crude product. A column separation process using a solvent (CHCl3:MeOH=10:1) is performed, and the resultant is re-crystallized by using CHCl3 to obtain the compound A-7 (3.8 g).

5. Synthesis of Compound A-10

[Reaction Formula 5]

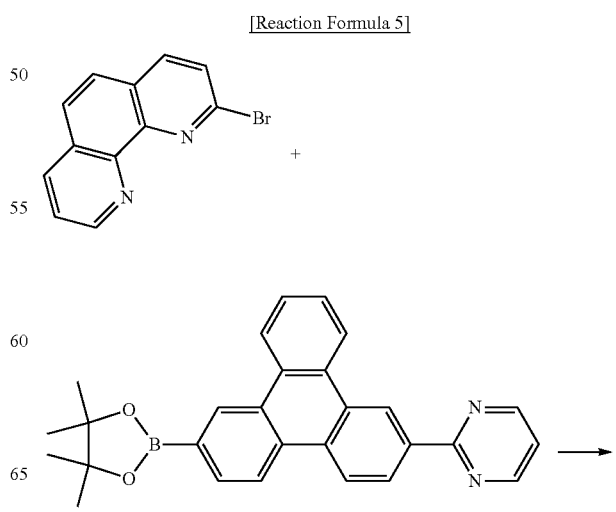

-continued

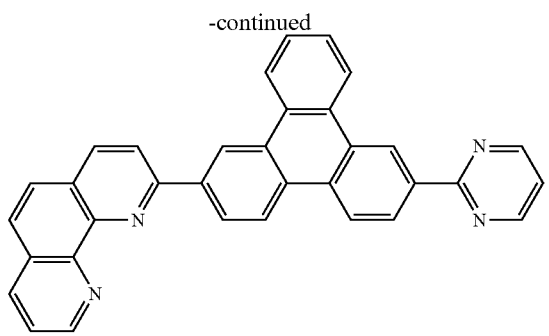

2-bromo-1,10-phenanthroline(5 g, 0.02 mol), 2-(2-(4,4,5,5-tetramethyl-1,3,2-dioxaborolan-2-yl)triphenylen-7-yl)pyrimidine(7.2 g, 0.02 mol), tetrakis(triphenylphosphine)palladium(0) (0.7 g, 0.06 mmol), toluene (150 ml), ethanol (20 ml) and 4M K2CO3 (8 ml) were refluxed and stirred for about 12 hours in the round bottom flask. After completion of the reaction, the reacting solution was filtered to obtain a crude product. A column separation process using a solvent (CHCl3:MeOH=10:1) is performed, and the resultant is re-crystallized by using CHCl3 to obtain the compound A-10 (3.6 g).

6. Synthesis of Compound A-20

(1) Compound B-4

[Reaction Formula 6-1]

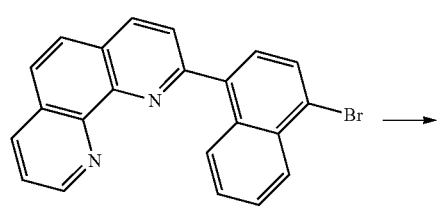

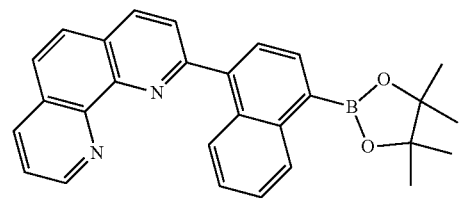

The compound B-2 (10 g, 0.075 mol), bis(pinacolato) diboron (7.9 g, 0.04 mol), [1,1'-bis(diphenylphosphino)ferrocene]dichloropalladium(II) (1.1 g, 0.2 mmol), KOAc (9.2 g, 0.09 mol) and 1,4-dioxane (200 ml) were input into the round bottom flask, and a temperature was increased. The mixture was refluxed and stirred for about 12 hours. The solution was cooled into the room temperature and filtered by using celite. Then, the celite was washed by CHCl3. The remaining solution was concentrated under the reduced pressure and re-crystalized by using ethylene acetate such that the compound B-4 (2-(1-(4,4,5,5-tetramethyl-1,3,2-dioxaborolan-2-yl)naphthalen-4-yl)-1,10-phenanthroline, 7.9 g) is obtained.

(2) Compound A-20

[Reaction Formula 6-2]

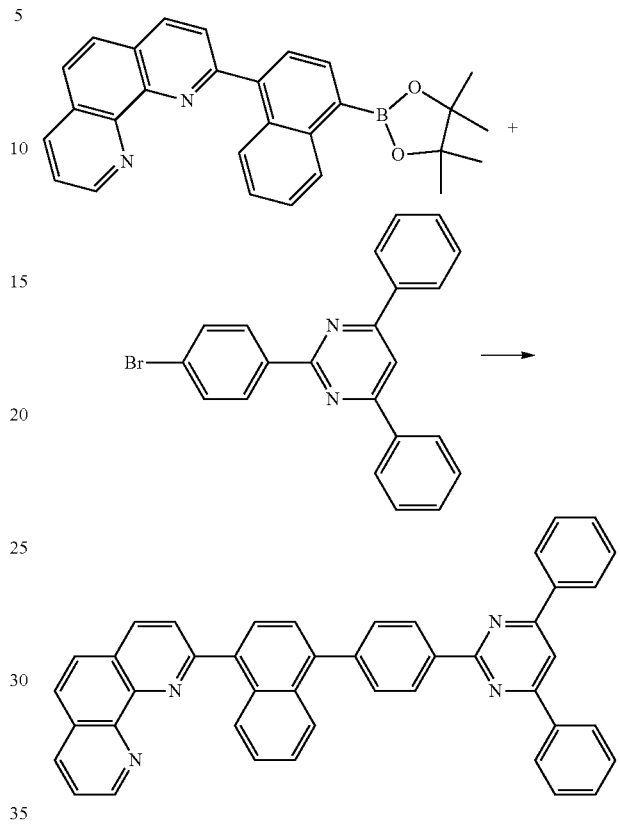

The compound B-4 (5 g, 0.01 mol), 2-(4-bromophenyl)-4,6-diphenylpyrimidine(5.4 g, 0.01 mol), tetrakis(triphenylphosphine)palladium(0) (0.5 g, 0.05 mmol), toluene 100 ml, ethanol (20 ml) and 4M K2CO3 (6 ml) were refluxed and stirred for about 12 hours in the round bottom flask. After completion of the reaction, the reacting solution was filtered to obtain a crude product. A column separation process using a solvent (CHCl3:MeOH=10:1) is performed, and the resultant is re-crystallized by using CHCl3 to obtain the compound A-20 (3.9 g).

7. Synthesis of Compound A-24

[Reaction Formula 7]

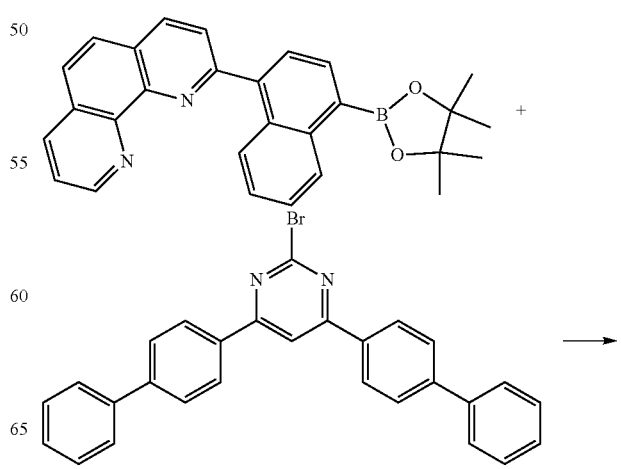

-continued

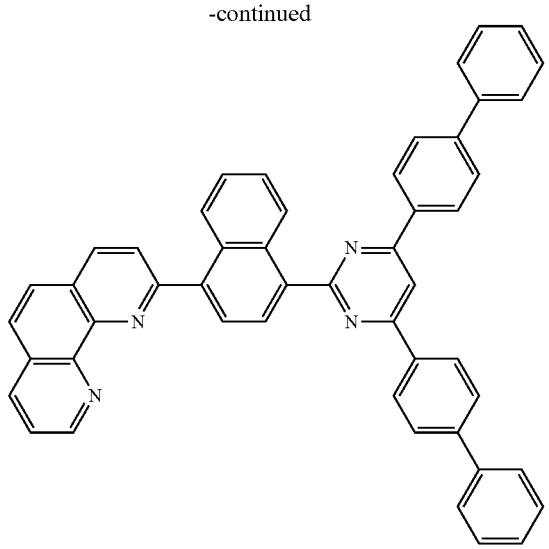

The compound B-4 (5 g, 0.01 mol), 2-bromo-4,6-(bisbiphenyl-4-yl)pyrimidine (5.9 g, 0.01 mol), tetrakis(triphenylphosphine)palladium(0) (0.5 g, 0.05 mmol), toluene 100 ml, ethanol (20 ml) and 4M K2CO3 (6 ml) were refluxed and stirred for about 12 hours in the round bottom flask. After completion of the reaction, the reacting solution was filtered to obtain a crude product. A column separation process using a solvent (CHCl3:MeOH=10:1) is performed, and the resultant is re-crystallized by using CHCl3 to obtain the compound A-24 (4.0 g).

8. Synthesis of Compound A-35

[Reaction Formula 8]

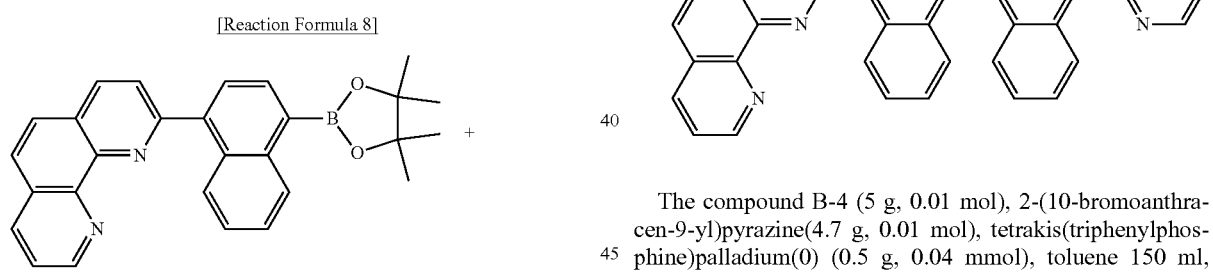

The compound B-4 (5 g, 0.01 mol), 5-(10-bromoanthracen-9-yl)-2-phenylpyrimidine(5.7 g, 0.01 mol), tetrakis(triphenylphosphine)palladium(0) (0.5 g, 0.05 mmol), toluene 150 ml, ethanol (20 ml) and 4M K2CO3 (6 ml) were refluxed and stirred for about 12 hours in the round bottom flask. After completion of the reaction, the reacting solution was filtered to obtain a crude product. A column separation process using a solvent (CHCl3:MeOH=10:1) is performed, and the resultant is re-crystallized by using CHCl3 to obtain the compound A-35 (3.8 g).

9. Synthesis of Compound A-40

[Reaction Formula 9]

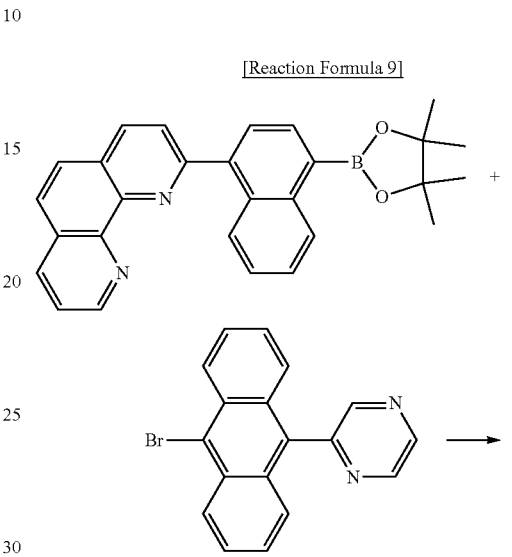

The compound B-4 (5 g, 0.01 mol), 2-(10-bromoanthracen-9-yl)pyrazine(4.7 g, 0.01 mol), tetrakis(triphenylphosphine)palladium(0) (0.5 g, 0.04 mmol), toluene 150 ml, ethanol (20 ml) and 4M K2CO3 (6 ml) were refluxed and stirred for about 12 hours in the round bottom flask. After completion of the reaction, the reacting solution was filtered to obtain a crude product. A column separation process using a solvent (CHCl3:MeOH=10:1) is performed, and the resultant is re-crystallized by using CHCl3 to obtain the compound A-40 (3.2 g).

10. Synthesis of Compound A-42

[Reaction Formula 10]

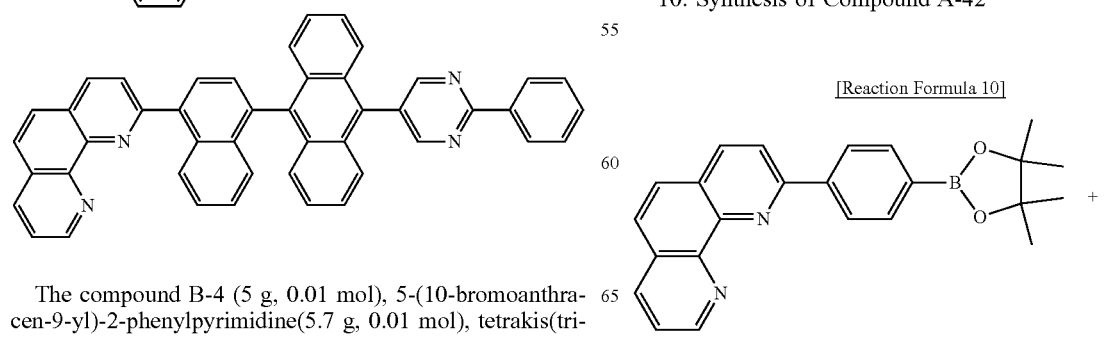

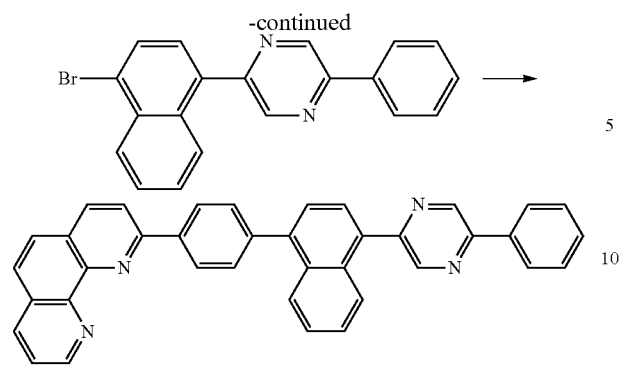

The compound B-3 (5 g, 0.01 mol), 2-(1-bromonaphthalen-4-yl)-5-phenylpyrazine (5.7 g, 0.02 mol), tetrakis(triphenylphosphine)palladium(0) (0.6 g, 0.05 mmol), toluene 100 ml, ethanol (20 ml) and 4M K2CO3 (7 ml) were refluxed and stirred for about 12 hours in the round bottom flask. After completion of the reaction, the reacting solution was filtered to obtain a crude product. A column separation process using a solvent (CHCl3:MeOH=10:1) is performed, and the resultant is re-crystallized by using methylene dichloride to obtain the compound A-42 (3.8 g).

11. Synthesis of Compound A-48

[Reaction Formula 11]

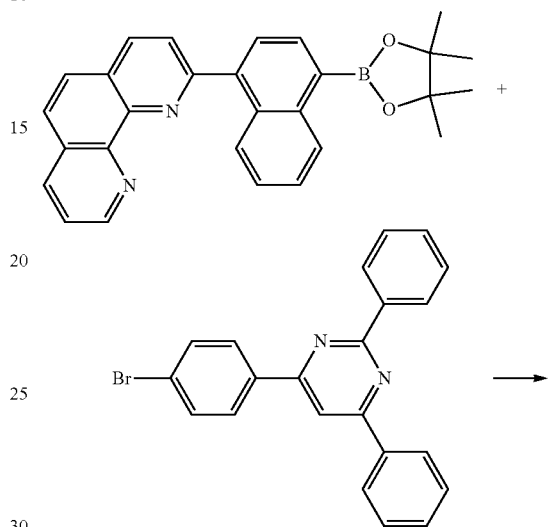

The compound B-3 (5 g, 0.01 mol), 4-(4-bromophenyl)-2,6-diphenylpyrimidine(6.1 g, 0.02 mol), tetrakis(triphenylphosphine)palladium(0) (0.6 g, 0.05 mmol), toluene 100 ml, ethanol (20 ml) and 4M K2CO3 (7 ml) were refluxed and stirred for about 12 hours in the round bottom flask. After completion of the reaction, the reacting solution was filtered to obtain a crude product. A column separation process using a solvent (CHCl3:MeOH=10:1) is performed, and the resultant is re-crystallized by using methylene dichloride to obtain the compound A-48 (3.9 g).

12. Synthesis of Compound A-49

[Reaction Formula 12]

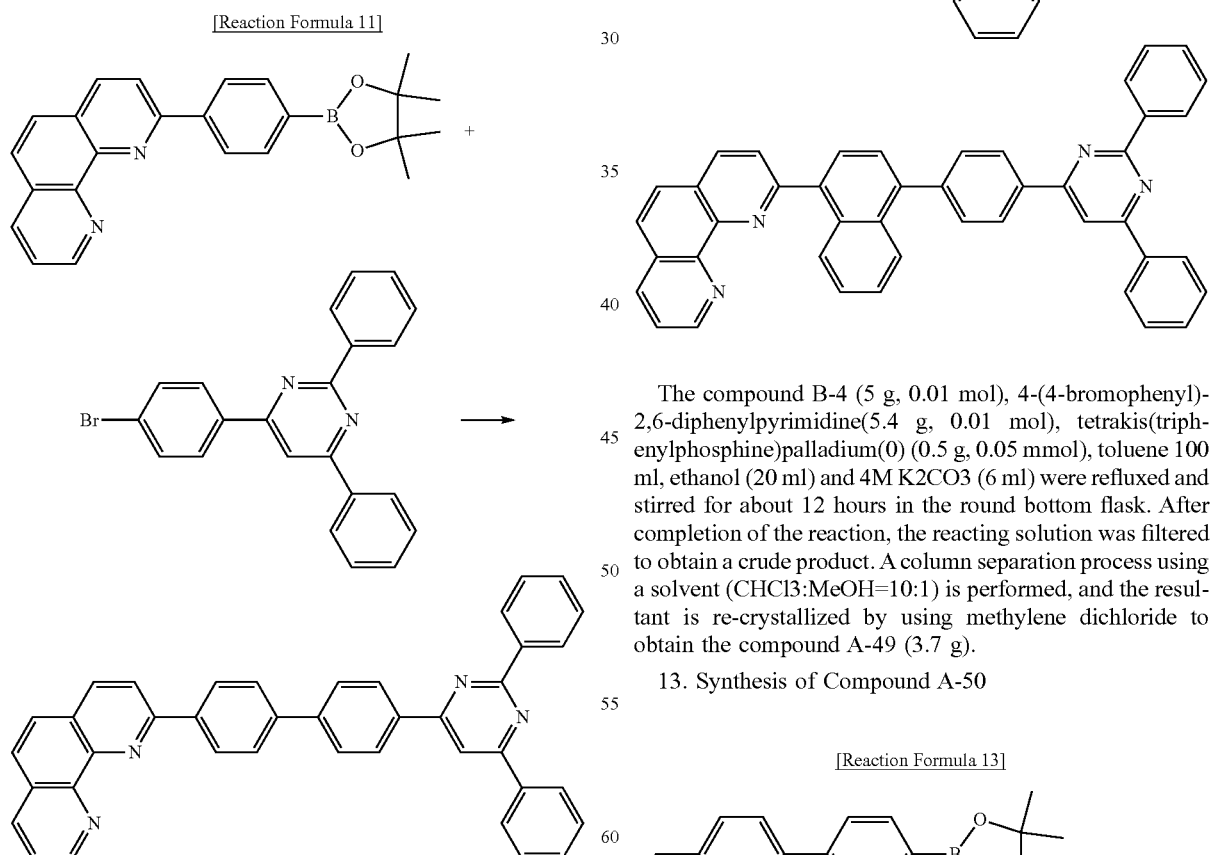

The compound B-4 (5 g, 0.01 mol), 4-(4-bromophenyl)-2,6-diphenylpyrimidine(5.4 g, 0.01 mol), tetrakis(triphenylphosphine)palladium(0) (0.5 g, 0.05 mmol), toluene 100 ml, ethanol (20 ml) and 4M K2CO3 (6 ml) were refluxed and stirred for about 12 hours in the round bottom flask. After completion of the reaction, the reacting solution was filtered to obtain a crude product. A column separation process using a solvent (CHCl3:MeOH=10:1) is performed, and the resultant is re-crystallized by using methylene dichloride to obtain the compound A-49 (3.7 g).

13. Synthesis of Compound A-50

[Reaction Formula 13]

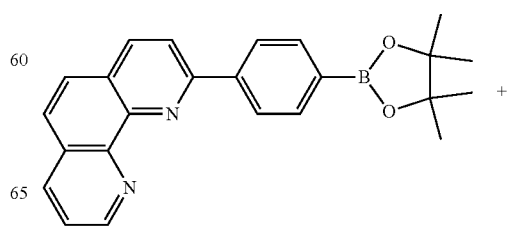

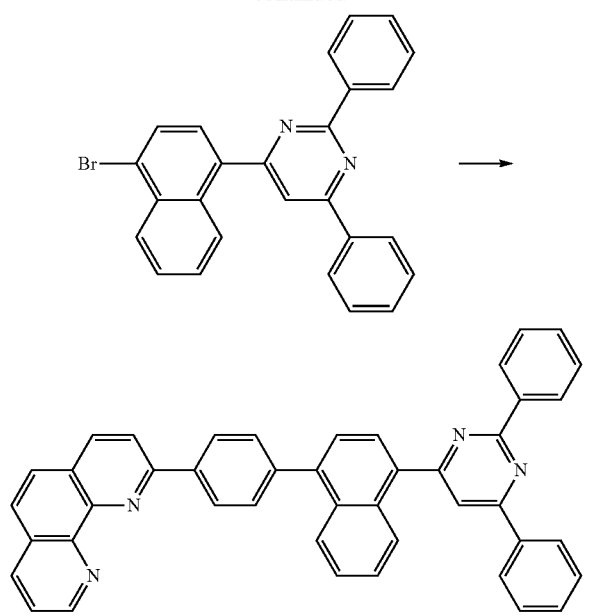

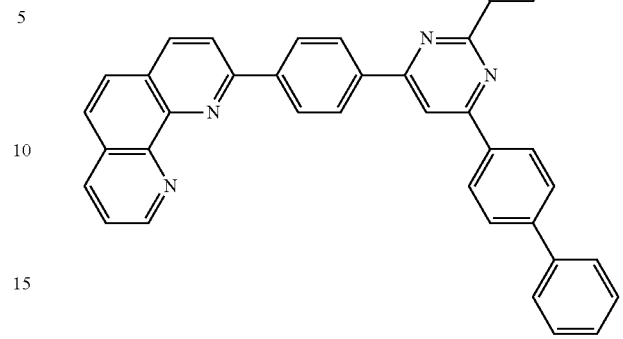

The compound B-3 (5 g, 0.01 mol), 4-(1-bromonaphthalen-4-yl)-2,6-diphenylpyrimidine(6.9 g, 0.02 mol), tetrakis(triphenylphosphine)palladium(0) (0.6 g, 0.05 mmol), toluene 100 ml, ethanol (20 ml) and 4M K2CO3 (7 ml) were refluxed and stirred for about 12 hours in the round bottom flask. After completion of the reaction, the reacting solution was filtered to obtain a crude product. A column separation process using a solvent (CHCl3:MeOH=10:1) is performed, and the resultant is re-crystallized by using methylene dichloride to obtain the compound A-50 (4.2 g).

14. Synthesis of Compound A-51

[Reaction Formula 14]

The compound B-3 (5 g, 0.01 mol), 4-bromo-2-phenyl-6-(biphenyl-4-yl)pyrimidine(6.1 g, 0.02 mol), tetrakis(triphenylphosphine)palladium(0) (0.6 g, 0.05 mmol), toluene 100 ml, ethanol (20 ml) and 4M K2CO3 (7 ml) were refluxed and stirred for about 12 hours in the round bottom flask. After completion of the reaction, the reacting solution was filtered to obtain a crude product. A column separation process using a solvent (CHCl3:MeOH=10:1) is performed, and the resultant is re-crystallized by using methylene dichloride to obtain the compound A-51 (3.9 g).

15. Synthesis of Compound A-62

[Reaction Formula 15]

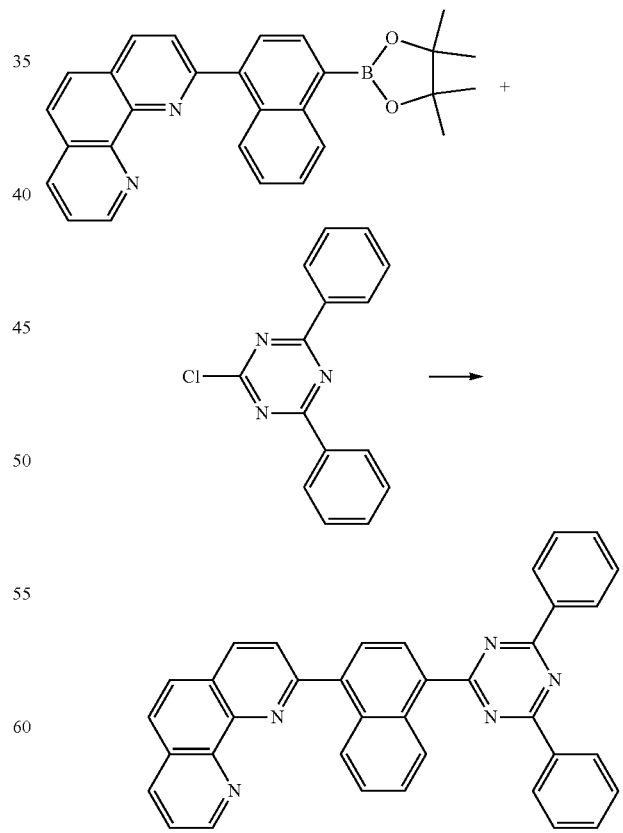

The compound B-4 (5 g, 0.01 mol), 2-chloro-4,6-diphenyl-1,3,5-triazine(3.7 g, 0.01 mol), tetrakis(triphenylphosphine)palladium(0) (0.5 g, 0.05 mmol), toluene 100 ml, ethanol (20 ml) and 4M K2CO3 (6 ml) were refluxed and stirred for about 12 hours in the round bottom flask. After completion of the reaction, the reacting solution was filtered to obtain a crude product. A column separation process using a solvent (CHCl3:MeOH=10:1) is performed, and the resultant is re-crystallized by using methylene dichloride to obtain the compound A-62 (2.8 g).

16. Synthesis of Compound A-63

17. Synthesis of Compound A-67

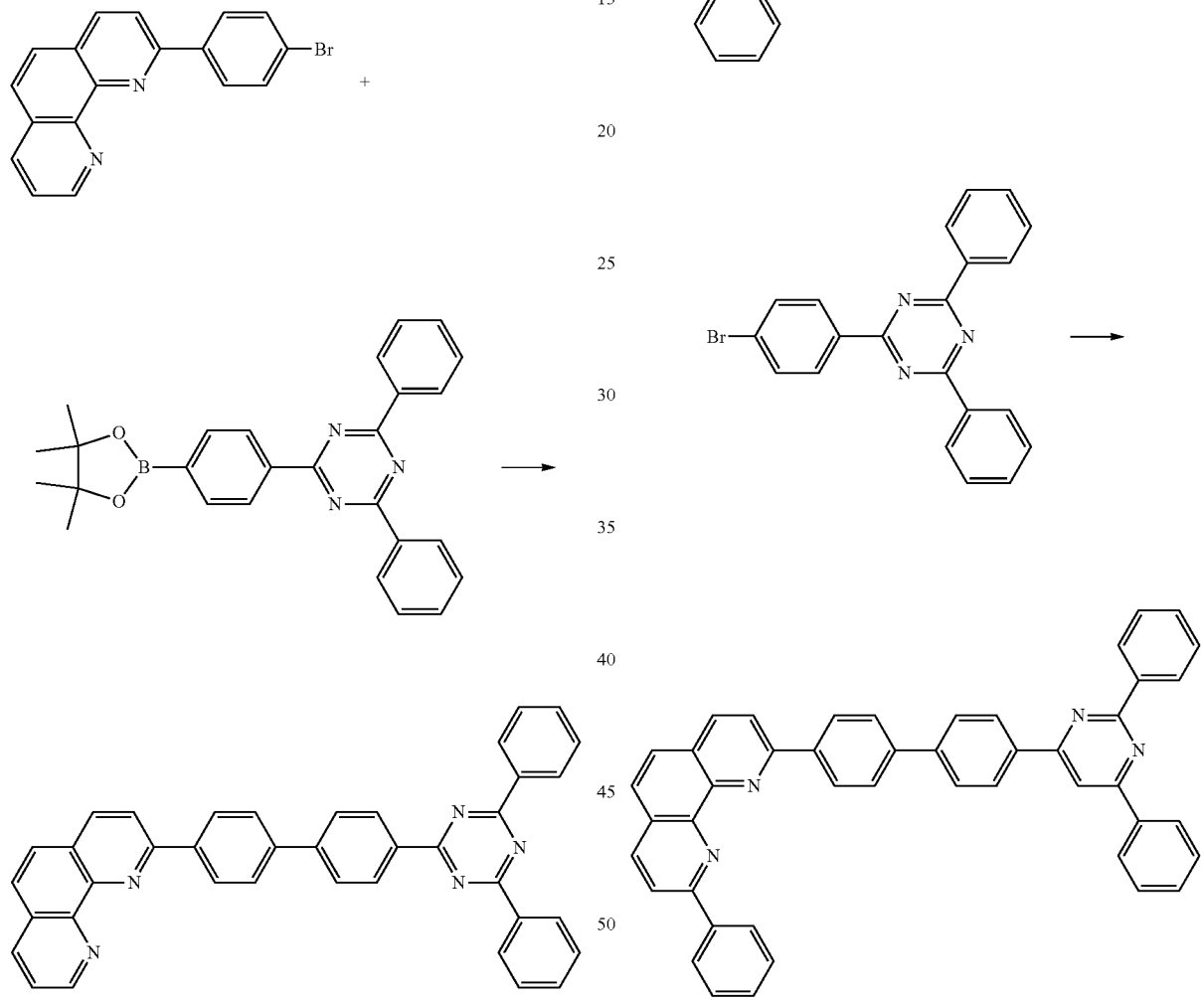

The compound B-1 (5 g, 0.03 mol), 2-(4-(4,4,5,5-tetramethyl-1,3,2-dioxaborolan-2-yl)phenyl)-4,6-diphenyl-1,3,5-triazine(7.8 g, 0.02 mol), tetrakis(triphenylphosphine)palladium(0) (0.7 g, 0.06 mmol), toluene 100 ml, ethanol (20 ml) and 4M K2CO3 (7 ml) were refluxed and stirred for about 12 hours in the round bottom flask. After completion of the reaction, the reacting solution was filtered to obtain a crude product. A column separation process using a solvent (CHCl3:MeOH=10:1) is performed, and the resultant is re-crystallized by using methylene dichloride to obtain the compound A-63 (3.8 g).

2-(4-(4,4,5,5-tetramethyl-1,3,2-dioxaborolan-2-yl)phenyl)-9-phenyl-1,10-phenanthroline (5 g, 0.01 mol), 4-(4-bromophenyl)-2,6-diphenylpyrimidine (5.1 g, 0.01 mol), tetrakis(triphenylphosphine)palladium(0) (0.5 g, 0.04 mmol), toluene 150 ml, ethanol (20 ml) and 4M K2CO3 (6 ml) were refluxed and stirred for about 12 hours in the round bottom flask. After completion of the reaction, the reacting solution was filtered to obtain a crude product. A column separation process using a solvent (CHCl3:MeOH=10:1) is performed, and the resultant is re-crystallized by using CHCl3 to obtain the compound A-67 (4.2 g).

18. Synthesis of Compound A-68

[Reaction Formula 18]

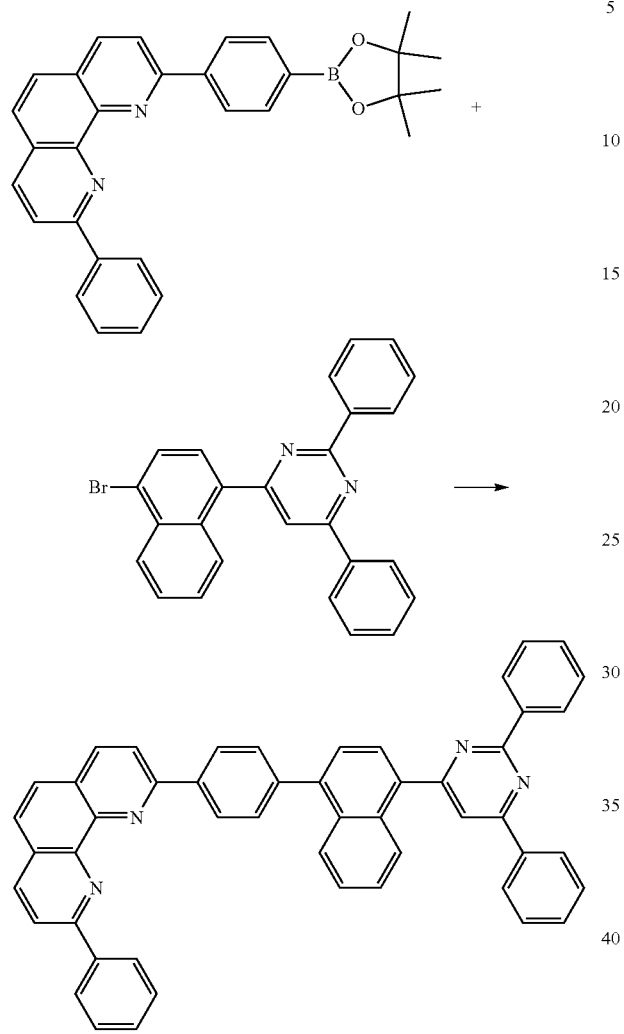

2-(4-(4,4,5,5-tetramethyl-1,3,2-dioxaborolan-2-yl)phenyl)-9-phenyl-1,10-phenanthroline (5 g, 0.01 mol), 4-(1-bromonaphthalen-4-yl)-2,6-diphenylpyrimidine (5.7 g, 0.01 mol), tetrakis(triphenylphosphine)palladium(0) (0.5 g, 0.04 mmol), toluene 150 ml, ethanol (20 ml) and 4M K2CO3 (6 ml) were refluxed and stirred for about 12 hours in the round bottom flask. After completion of the reaction, the reacting solution was filtered to obtain a crude product. A column separation process using a solvent (CHCl3:MeOH=10:1) is performed, and the resultant is re-crystallized by using CHCl3 to obtain the compound A-68 (3.8 g).

Organic Light Emitting Diode

1. Comparative Example (Ref)

An ITO layer is deposited and patterned on a substrate and washed to form the anode (2 mm*2 mm). The substrate is loaded in a vacuum chamber having a base pressure of 5~7*10-8, and layers are sequentially deposited as below.

(1) the HIL (NPD and F4-TCNQ (10 wt % doping), 100 Å), (2) the first HTL (NPD, 1200 Å), (3) the first (blue) EML (anthracene host and pyrene dopant (4 wt % doping), 200 Å), (4) the first ETL (TmPyPB, 100 Å), (5) the N-type CGL (BPhene and Li (2 wt % doping), 100 Å), (6) the P-type CGL (NPD and F4-TCNQ (10 wt % doping), 200 Å), (7) the second HTL (NPD, 200 Å), (8) the second (yellow) EML (CBP host and Ir dopant (10 wt % doping), 200 Å), (9) the second ETL (Alq3, 100 Å), (10) the EIL (LiF, 5 Å) and (11) the cathode (Al, 2000 Å).

2. EXAMPLES (1) Example 1 (Compound A-4)

The organic light emitting diode of "Example 1" is provided using the compound A-4 into the first ETL instead of the material of the first ETL in "Comparative Example".

(2) Example 2 (Compound A-7)

The organic light emitting diode of "Example 2" is provided using the compound A-7 into the first ETL instead of the material of the first ETL in "Comparative Example".

(3) Example 3 (Compound A-24)

The organic light emitting diode of "Example 3" is provided using the compound A-24 into the first ETL instead of the material of the first ETL in "Comparative Example".

(4) Example 4 (Compound A-48)

The organic light emitting diode of "Example 4" is provided using the compound A-48 into the first ETL instead of the material of the first ETL in "Comparative Example".

(5) Example 5 (Compound A-62)

The organic light emitting diode of "Example 5" is provided using the compound A-62 into the first ETL instead of the material of the first ETL in "Comparative Example".

The driving voltage, the external quantum efficiency (EQE) and the lifetime of the organic light emitting diodes of "Comparative Example" and "Example 1" to "Example 5" are measured and listed in Table 1. The current density, the EQE and the lifetime are shown in FIGS. 3A to 3C.

TABLE 1

|  | voltage [%] | EQE [%] | lifetime [%] |
|---|---|---|---|
| Ref | 100 | 100 | 100 |
| A-4 | 106 | 102 | 102 |
| A-7 | 106 | 96 | 156 |
| A-24 | 104 | 99 | 108 |
| A-48 | 100 | 102 | 119 |
| A-62 | 100 | 99 | 144 |

Figure 3A:
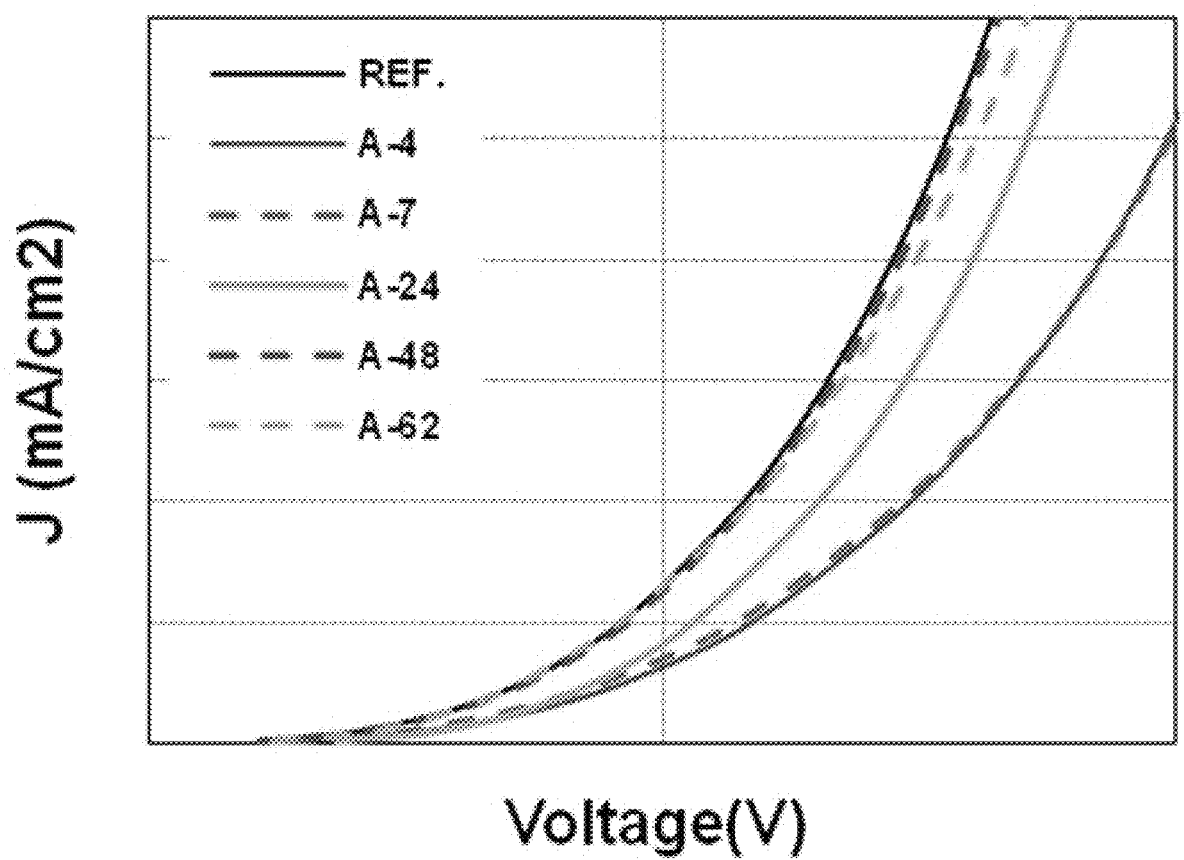
FIGS. 3A to 3C are graphs showing emitting properties of an organic light emitting diode including an organic compound in an electron transporting layer.
Figure 3B:
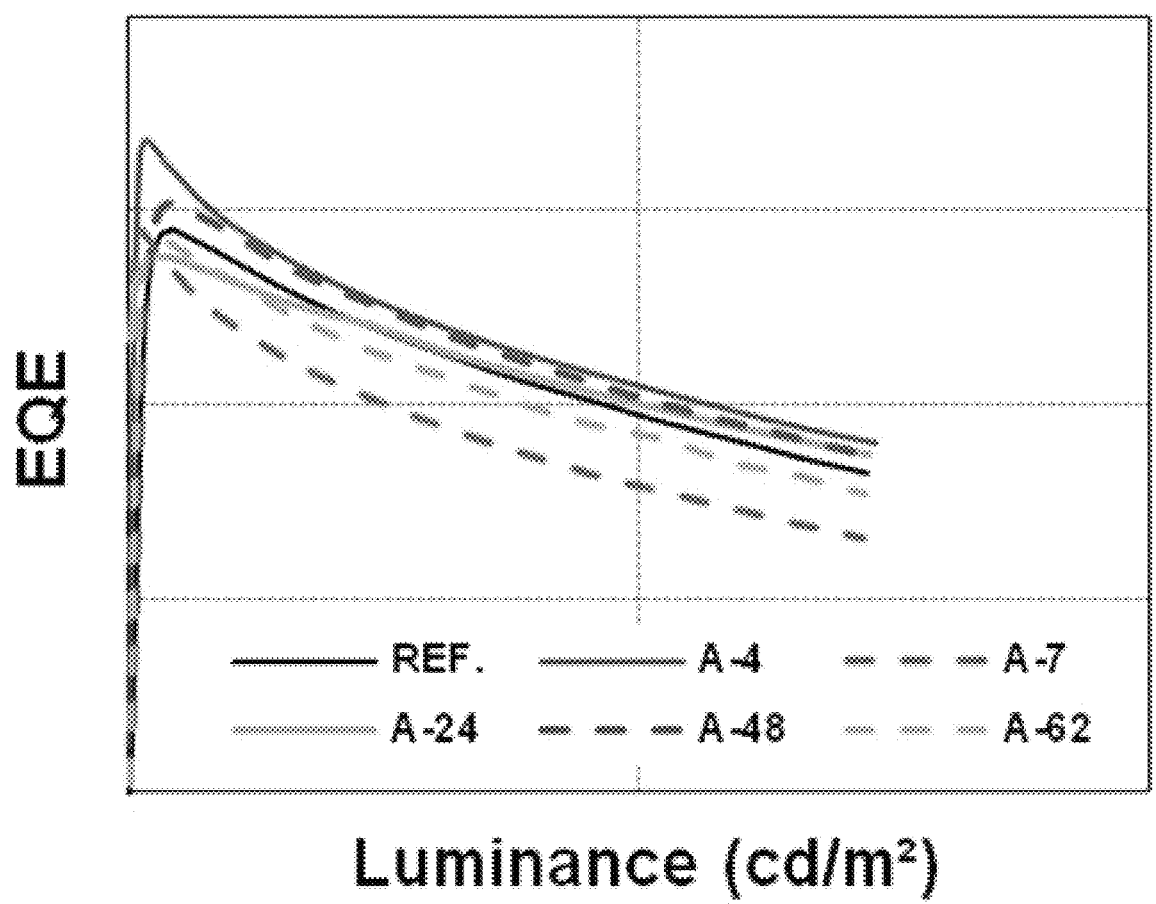
Figure 3C:
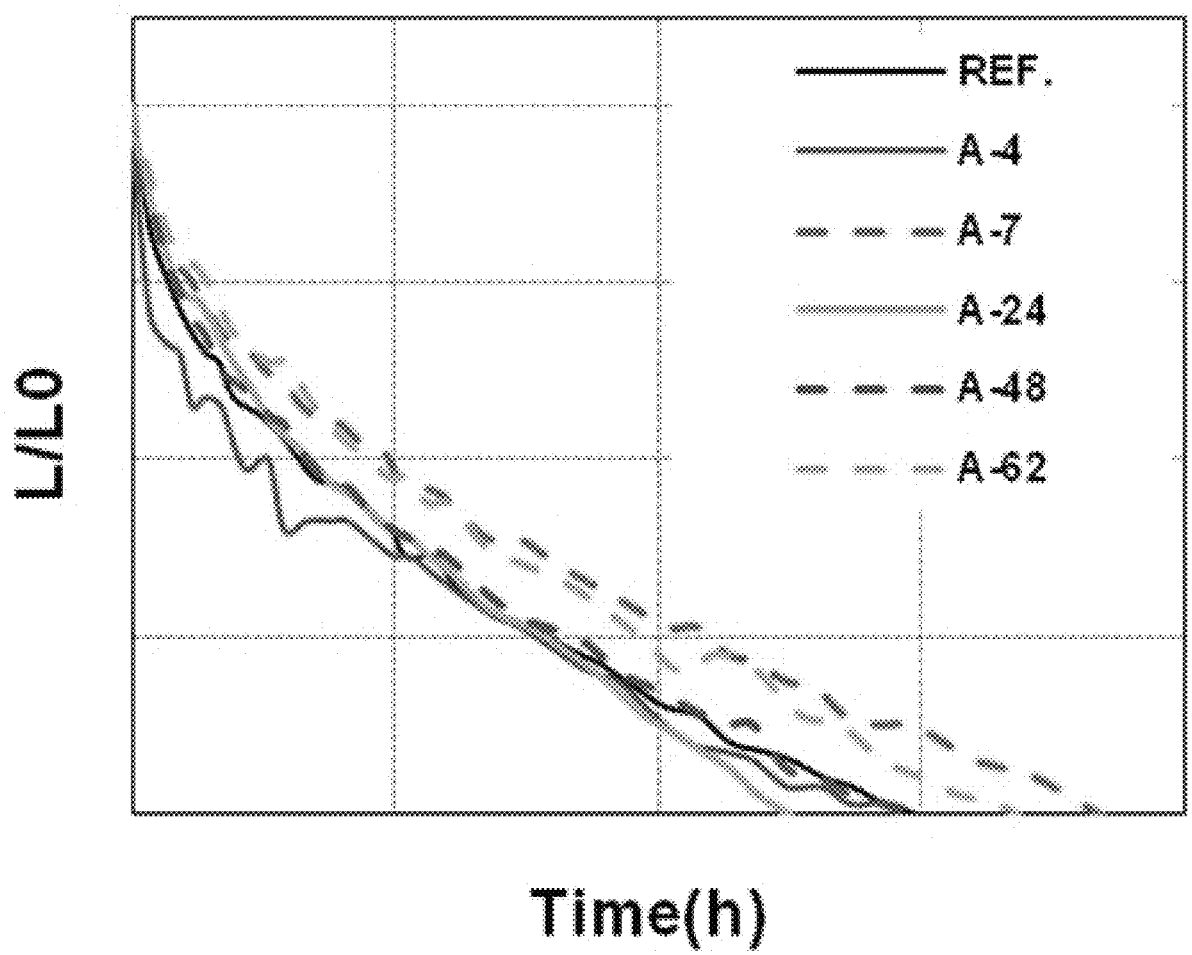

As shown in Table 1 and FIGS. 3A to 3C, in comparison to "Comparative Example", all of the EQE and the lifetime of the organic light emitting diode using the organic compound of the present invention in the first ETL are improved or at least one of the EQE and the lifetime of the organic light emitting diode using the organic compound of the present invention in the first ETL is remarkably improved.

For example, all of the EQE and the lifetime of the organic light emitting diode using the compound A-4 in the first ETL are increased. On the other hand, in the organic light emitting diode using the compound A-7 in the first ETL, although the EQE is slightly decreased, the lifetime is remarkably increased.

3. EXAMPLES

(1) Example 6 (Compound A-2)

The organic light emitting diode of "Example 6" is provided using the compound A-2 into the N-type CGL instead of the material of the N-type CGL in "Comparative Example".

(2) Example 7 (Compound A-10)

The organic light emitting diode of "Example 7" is provided using the compound A-10 into the N-type CGL instead of the material of the N-type CGL in "Comparative Example".

(3) Example 8 (Compound A-40)

The organic light emitting diode of "Example 8" is provided using the compound A-40 into the N-type CGL instead of the material of the N-type CGL in "Comparative Example".

(4) Example 9 (Compound A-49)

The organic light emitting diode of "Example 9" is provided using the compound A-49 into the N-type CGL instead of the material of the N-type CGL in "Comparative Example".

(5) Example 10 (Compound A-50)

The organic light emitting diode of "Example 10" is provided using the compound A-50 into the N-type CGL instead of the material of the N-type CGL in "Comparative Example".

(6) Example 11 (Compound A-52)

The organic light emitting diode of "Example 11" is provided using the compound A-52 into the N-type CGL instead of the material of the N-type CGL in "Comparative Example".

(7) Example 12 (Compound A-67)

The organic light emitting diode of "Example 12" is provided using the compound A-67 into the N-type CGL instead of the material of the N-type CGL in "Comparative Example".

(8) Example 13 (Compound A-68)

The organic light emitting diode of "Example 13" is provided using the compound A-68 into the N-type CGL instead of the material of the N-type CGL in "Comparative Example".

The driving voltage, the external quantum efficiency (EQE) and the lifetime of the organic light emitting diodes of "Comparative Example" and "Example 6" to "Example 13" are measured and listed in Table 2. The current density, the EQE and the lifetime are shown in FIGS. 4A to 4C.

TABLE 2

|      | voltage [%] | EQE [%] | lifetime [%] |
|------|-------------|---------|--------------|
| Ref  | 100         | 100     | 100          |
| A-2  | 105         | 101     | 117          |
| A-10 | 106         | 93      | 192          |
| A-40 | 100         | 97      | 132          |
| A-49 | 100         | 101     | 143          |
| A-50 | 98          | 96      | 109          |
| A-52 | 100         | 99      | 129          |
| A-67 | 98          | 100     | 110          |
| A-68 | 98          | 101     | 156          |

Figure 4B:
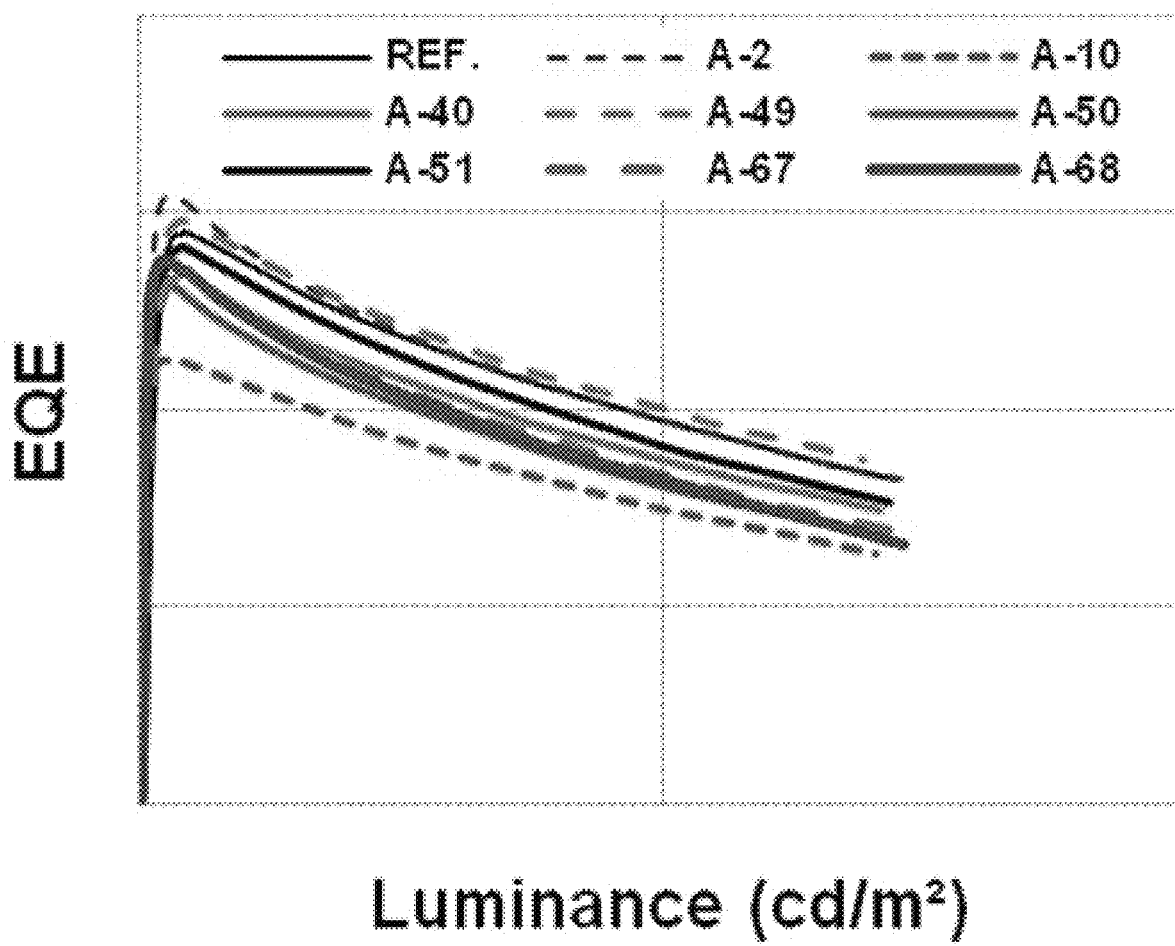

As shown in Table 2 and FIGS. 4A to 4C, in comparison to "Comparative Example", all of the EQE and the lifetime of the organic light emitting diode using the organic compound of the present invention in the N-CGL are improved or at least one of the EQE and the lifetime of the organic light emitting diode using the organic compound of the present invention in the N-CGL is remarkably improved.

For example, all of the EQE and the lifetime of the organic light emitting diode using the compound A-2 in the N-CGL are increased. On the other hand, in the organic light emitting diode using the compound A-10 in the N-CGL, although the EQE is slightly decreased, the lifetime is remarkably increased.

As mentioned above, the organic compound of the present invention includes the phenanthroline core having the nitrogen atom of a relatively electron rich sp2 hybrid orbital such that the organic compound has excellent electron transporting property.

In addition, the nitrogen atom of the organic compound is combined or bound with the alkali metal or the alkali earth metal as a dopant in the N-type CGL to form a gap state such that an electron transporting property from the N-type CGL into the ETL is improved.

Moreover, since the alkali metal or the alkali earth metal is combined with the nitrogen atom in the organic compound, the diffusion of the alkali metal or the alkali earth metal into the P-type CGL is prevented.

Accordingly, when the organic compound of the present invention is used for the N-type CGL and/or the ETL of the organic light emitting diode, the organic light emitting diode and the OLED device have advantages in the driving voltage, the emitting efficiency and the lifetime.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:
1. An organic compound, represented by following Formula:

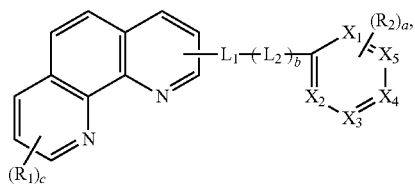

wherein each of $X_1$ to $X_5$ is independently selected from a carbon atom or a nitrogen atom, and two of $X_1$ to $X_5$ are N, wherein each of $R_1$ and $R_2$ is independently selected from a substituted aryl group, a non-substituted aryl group, a substituted heteroaryl group or a non-substituted heteroaryl group, wherein a is an integer between 1 to 3, and c is 0 or 1, and wherein $L_1$ and $L_2$ are phenylene, and b is 1.

2. The organic compound according to claim 1, wherein each of $R^1$ and $R_2$ is one of phenyl, alkylphenyl, biphenyl, alkylbiphenyl, halophenyl, alkoxyphenyl, haloalkoxyphenyl, cyanophenyl, silylphenyl, naphthyl, alkylnaphthyl, halonaphthyl, cyanonaphthyl, silylnaphthyl, phenylnaphthyl, pyridyl, alkylpyridyl, halopyridyl, cyanopyridyl, alkoxypyridyl, silylpyridyl, phenylpyridyl, pyrimidyl, halopyrimidyl, cyanopyridimyl, alkoxypyrimidyl, phenylpyrimidyl, quinolinyl, isoquinolinyl, phenylquinolinyl, quinoxalinyl, pyrazinyl, quinazolinyl, naphthyridinyl, benzothiophenyl, benzofuranyl, dibenzothiophenyl, arylthiazolyl, dibenzofuranyl, fluorenyl, carbazoyl, imidazolyl, carbolinyl, phenanthrenyl, terphenyl, terpyridinyl, phenylterpyridinyl, triphenylenyl, fluoranthenyl and diazafluorenyl.

3. The organic compound according to claim 1, wherein the organic compound is selected from:

A-12

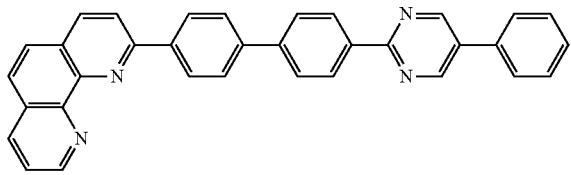

A-19

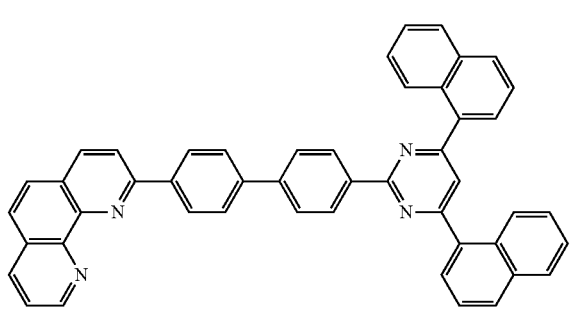

A-26

A-27

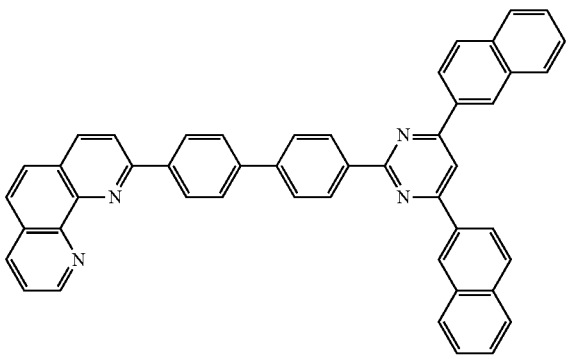

A-37

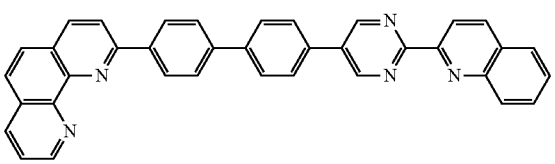

A-41

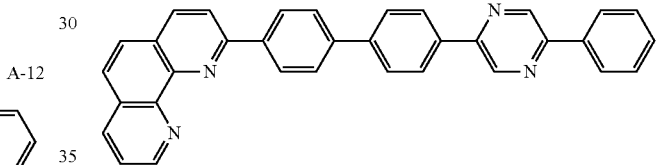

A-45

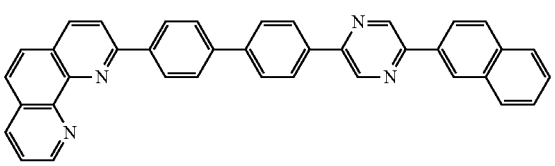

A-46

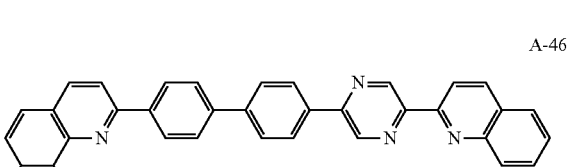

A-48

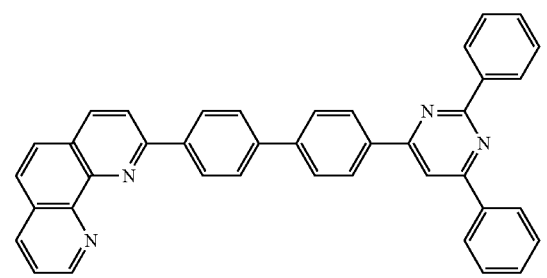

-continued

A-53

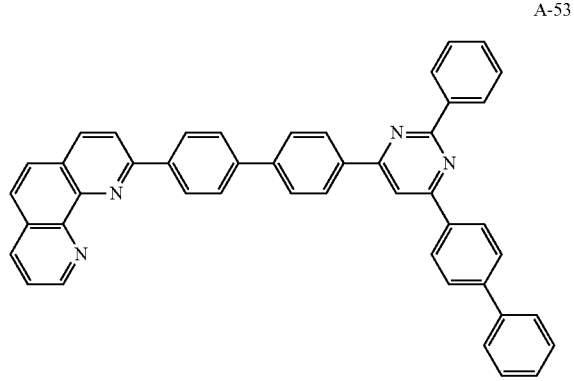

A-58

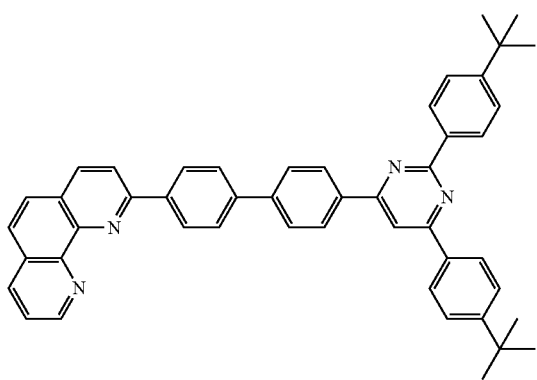

A-67

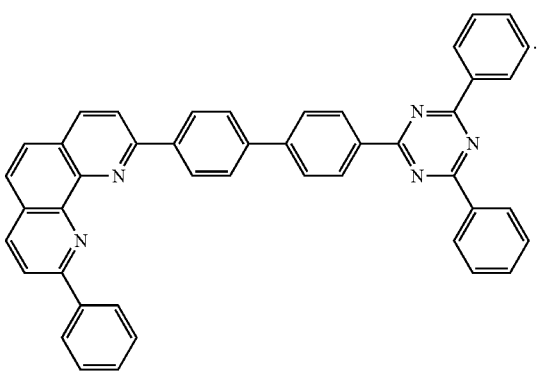

4. An organic light emitting diode, comprising:
first and second electrodes facing each other;
a first emitting part between the first and second electrodes, and including a first emitting material layer and an electron transporting layer;
a second emitting part between the first emitting part and the second electrode, and including a second emitting material layer; and
a charge generation layer between the first and second emitting parts,
wherein at least one of the electron transporting layer and the charge generation layer includes an organic compound represented by following Formula:

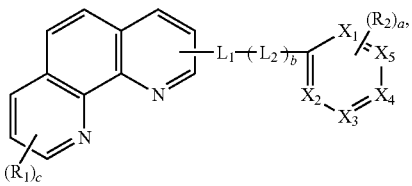

wherein each of $X_1$ to $X_5$ is independently selected from a carbon atom or a nitrogen atom, and two of $X_1$ to $X_5$ are N, wherein each of $R_1$ and $R_2$ is independently selected from a substituted aryl group, a non-substituted aryl group, a substituted heteroaryl group or a non-substituted heteroaryl group, wherein a is an integer between 1 to 3, and c is 0 or 1, and wherein $L_1$ and $L_2$ are phenylene, and b is 1.

5. The organic light emitting diode according to claim 4, wherein each of $R_1$ and $R_2$ is one of phenyl, alkylphenyl, biphenyl, alkylbiphenyl, halophenyl, alkoxyphenyl, haloalkoxyphenyl, cyanophenyl, silylphenyl, naphthyl, alkylnaphthyl, halonaphthyl, cyanonaphthyl, silylnaphthyl, phenylnaphthyl, pyridyl, alkylpyridyl, halopyridyl, cyanopyridyl, alkoxypyridyl, silylpyridyl, phenylpyridyl, pyrimidyl, halopyrimidyl, cyanopyridimyl, alkoxypyrimidyl, phenylpyrimidyl, quinolinyl, isoquinolinyl, phenylquinolinyl, quinoxalinyl, pyrazinyl, quinazolinyl, naphthyridinyl, benzothiophenyl, benzofuranyl, dibenzothiophenyl, arylthiazolyl, dibenzofuranyl, fluorenyl, carbazoyl, imidazolyl, carbolinyl, phenanthrenyl, terphenyl, terpyridinyl, phenylterpyridinyl, triphenylenyl, fluoranthenyl and diazafluorenyl.

6. The organic compound according to claim 4, wherein the organic compound is selected from:

A-12

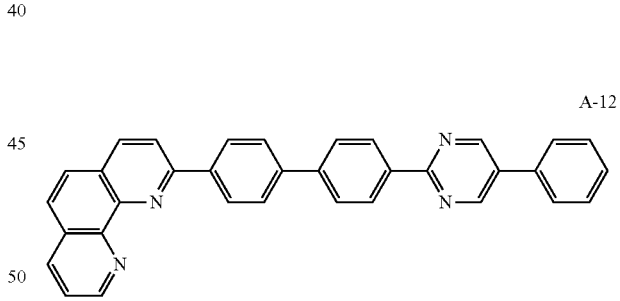

A-19

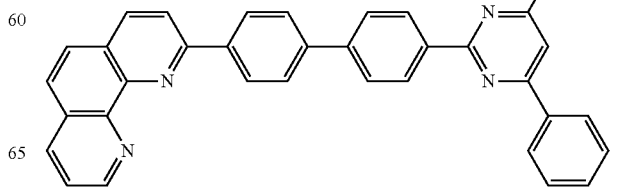

-continued

A-26
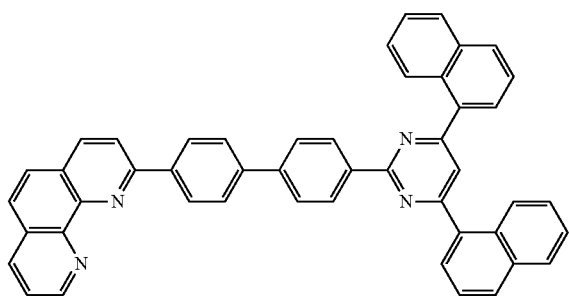

A-27
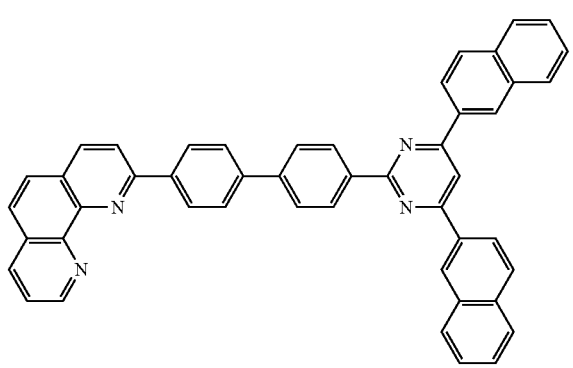

A-37
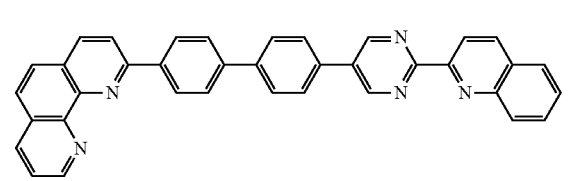

A-41
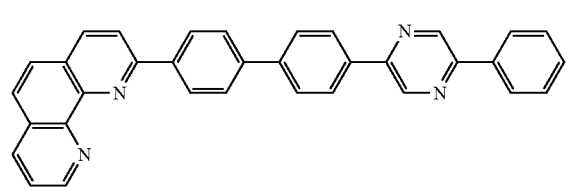

A-45
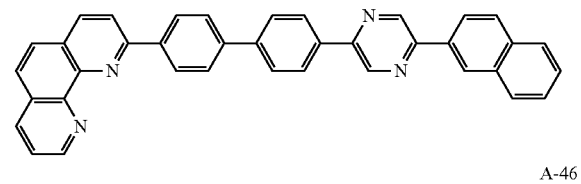

A-46
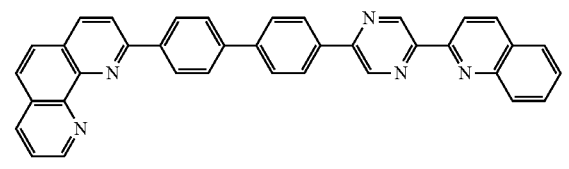

-continued

A-48
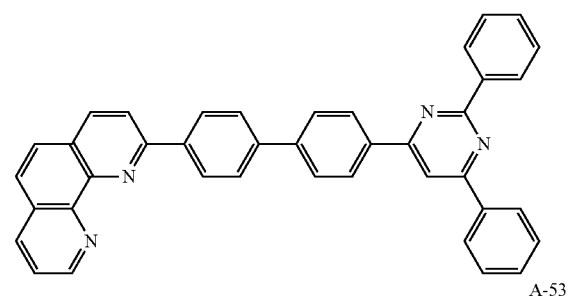

A-53

A-58

A-67

7. The organic light emitting diode according to claim 5, wherein one of the first and second emitting material layers emits a blue light, and the other one of the first and second emitting material layers emits a yellow-green light.

8. The organic light emitting diode according to claim 5, wherein the charge generation layer includes an N-type charge generation layer and a P-type charge generation layer, and the N-type charge generation layer includes an alkali metal or an alkali earth metal and the organic compound.

9. The organic light emitting diode according to claim 8, wherein the electron transporting layer is adjacent to the N-type charge generation layer.

10. An organic light emitting display device, comprising:
a substrate;
an organic light emitting diode over the substrate and including:
first and second electrodes facing each other,
a first emitting part between the first and second electrodes, and including a first emitting material layer and an electron transporting layer,
a second emitting part between the first emitting part, and the second electrode and including a second emitting material layer, and
a charge generation layer between the first and second emitting parts; and
a thin film transistor between the substrate and the organic light emitting diode and connected to the first electrode,
wherein at least one of the electron transporting layer and the charge generation layer includes an organic compound represented by following Formula:

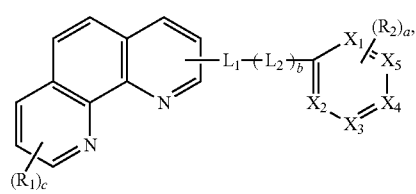

wherein each of $X_1$ to $X_5$ is independently selected from a carbon atom or a nitrogen atom, and two of $X_1$ to $X_5$ are N,
wherein each of $R_1$ and $R_2$ is independently selected from a substituted aryl group, a non-substituted aryl group, a substituted heteroaryl group or a non-substituted heteroaryl group,
wherein a is an integer between 1 to 3, and c is 0 or 1, and
wherein $L_1$ and $L_2$ are phenylene, and b is 1.

11. The organic light emitting display device according to claim 10, wherein each of $R_1$ and $R_2$ is one of phenyl, alkylphenyl, biphenyl, alkylbiphenyl, halophenyl, alkoxyphenyl, haloalkoxyphenyl, cyanophenyl, silylphenyl, naphthyl, alkylnaphthyl, halonaphthyl, cyanonaphthyl, silylnaphthyl, phenylnaphthyl, pyridyl, alkylpyridyl, halopyridyl, cyanopyridyl, alkoxypyridyl, silylpyridyl, phenylpyridyl, pyrimidyl, halopyrimidyl, cyanopyridimyl, alkoxypyrimidyl, phenylpyrimidyl, quinolinyl, isoquinolinyl, phenylquinolinyl, quinoxalinyl, pyrazinyl, quinazolinyl, naphthyridinyl, benzothiophenyl, benzofuranyl, dibenzothiophenyl, arylthiazolyl, dibenzofuranyl, fluorenyl, carbazoyl, imidazolyl, carbolinyl, phenanthrenyl, terphenyl, terpyridinyl, phenylterpyridinyl, triphenylenyl, fluoranthenyl and diazafluorenyl.

12. The organic light emitting display device according to claim 10, wherein the organic compound is selected from:

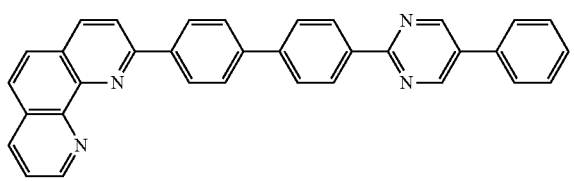

A-12

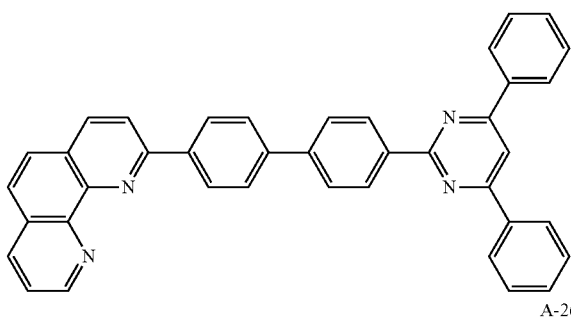

A-19

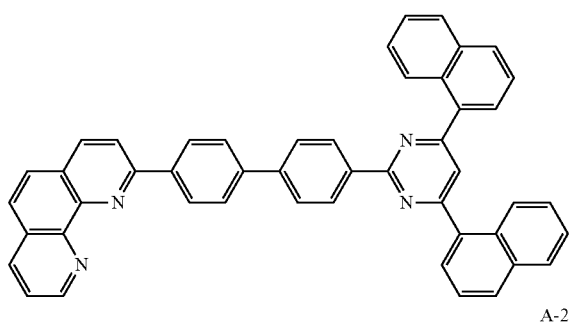

A-26

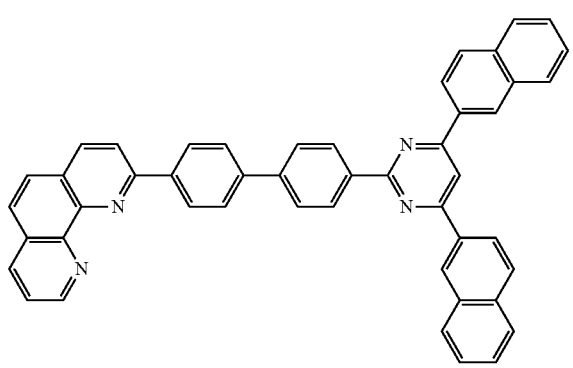

A-27

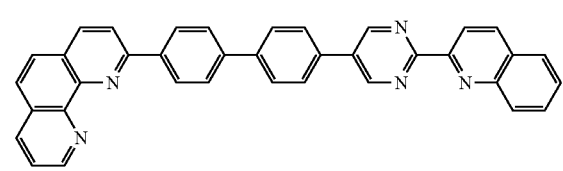

A-37

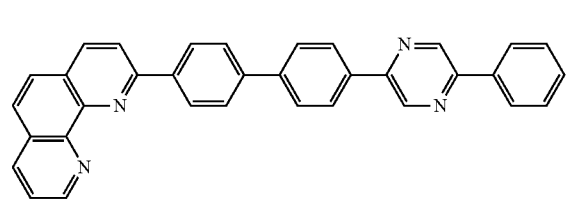

A-41

A-45

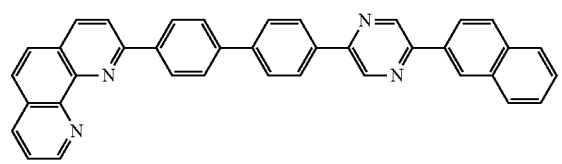

A-46

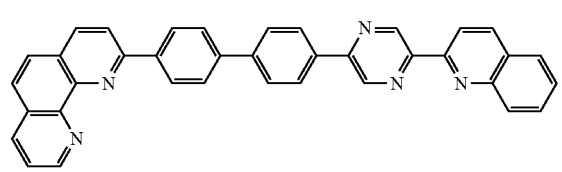

A-46

A-48

A-53

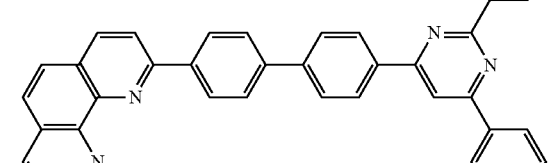

A-58

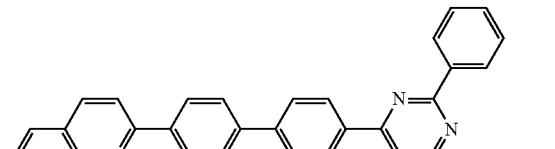

A-67

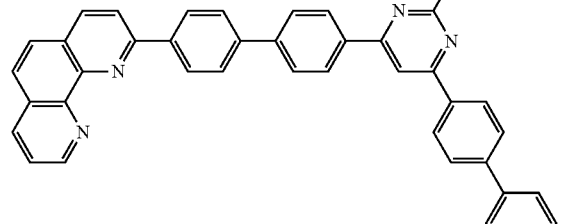

13. The organic light emitting display device according to claim 11, wherein one of the first and second emitting material layers emits a blue light, and the other one of the first and second emitting material layers emits a yellow-green light.

14. The organic light emitting display device according to claim 11, wherein the charge generation layer includes an N-type charge generation layer and a P-type charge generation layer, and the N-type charge generation layer includes an alkali metal or an alkali earth metal and the organic compound.

15. The organic light emitting display device according to claim 14, wherein the electron transporting layer is adjacent to the N-type charge generation layer.

16. The organic compound according to claim 1, wherein each of $X_1$ and $X_4$ is a nitrogen atom, and each of $X_2$, $X_3$ and $X_5$ is a carbon atom.

17. The organic light emitting diode according to claim 4, wherein each of $X^1$ and $X_4$ is a nitrogen atom, and each of $X_2$, $X_3$ and $X_5$ is a carbon atom.

18. The organic light emitting display device according to claim 10, wherein each of $X_1$ and $X_4$ is a nitrogen atom, and each of $X_2$, $X_3$ and $X_5$ is a carbon atom.

* * * * *